United States Patent
Hamamoto

(10) Patent No.: US 8,917,959 B2
(45) Date of Patent: Dec. 23, 2014

(54) ANALYZING ELEMENT AND ANALYZING APPARATUS USING SAME

(75) Inventor: Kiichi Hamamoto, Fukuoka (JP)

(73) Assignee: Denso Corporation, Aichi (JP)

( * ) Notice: Subject to any disclaimer, the term of this patent is extended or adjusted under 35 U.S.C. 154(b) by 1336 days.

(21) Appl. No.: 12/293,294

(22) PCT Filed: Mar. 16, 2007

(86) PCT No.: PCT/JP2007/000246
§ 371 (c)(1),
(2), (4) Date: Sep. 17, 2008

(87) PCT Pub. No.: WO2007/108214
PCT Pub. Date: Sep. 27, 2007

(65) Prior Publication Data
US 2009/0103852 A1    Apr. 23, 2009

(30) Foreign Application Priority Data
Mar. 17, 2006   (JP) ................. 2006-074435

(51) Int. Cl.
*G02B 6/00* (2006.01)
*A61B 5/097* (2006.01)
*G01N 21/03* (2006.01)
*G01N 33/497* (2006.01)

(52) U.S. Cl.
CPC .............. *G01N 21/031* (2013.01); *A61B 5/097* (2013.01); *G01N 33/497* (2013.01)
USPC .......................................................... 385/12

(58) Field of Classification Search
None
See application file for complete search history.

(56) References Cited

U.S. PATENT DOCUMENTS

| | | | | |
|---|---|---|---|---|
| 7,951,583 B2 * | 5/2011 | Duer | ............ | 435/288.7 |
| 8,187,866 B2 * | 5/2012 | Duer | ............ | 435/288.7 |
| 8,288,157 B2 * | 10/2012 | Duer | ............ | 435/288.7 |
| 8,675,199 B2 * | 3/2014 | Duer | ............ | 356/432 |
| 2006/0216200 A1 | 9/2006 | Nagatomo et al. | | |
| 2006/0252058 A1 | 11/2006 | Hayashi et al. | | |

FOREIGN PATENT DOCUMENTS

| | | |
|---|---|---|
| JP | 05-322747 | 12/1993 |
| JP | 06-281568 | 10/1994 |
| JP | 2002-148187 | 5/2002 |
| JP | 2003-279474 | 10/2003 |
| JP | 2005-218439 | 8/2005 |

(Continued)

OTHER PUBLICATIONS

Notification of Reason(s) for Refusal for Japanese Patent Application No. 2008-506176 Dated Mar. 19, 2013, 6 pgs.

(Continued)

*Primary Examiner* — Sung Pak
(74) *Attorney, Agent, or Firm* — Amin, Turocy & Watson, LLP

(57) ABSTRACT

An analyzing element (10) is provided with a sample chamber (11) into which a gas or liquid sample is introduced; detection light waveguides (12a, 12b) arranged adjacent to the sample chamber (11) for guiding detection light for detecting a sample; and a detection light inputting section (13) for inputting the detection light, which is traveling in a direction along the detection light waveguides (12a, 12b), into the detection light waveguides (12a, 12b) from the end surface of the detection light waveguides (12a, 12b). The detection light waveguides (12a, 12b) have an exposed surface (14) exposed in the sample chamber (11).

9 Claims, 9 Drawing Sheets

(56) References Cited

FOREIGN PATENT DOCUMENTS

| | | |
|---|---|---|
| JP | 2005-274208 | 10/2005 |
| JP | 2005-300212 | 10/2005 |
| JP | 2005-321244 | 11/2005 |
| JP | 2006-038816 | 2/2006 |
| JP | 2006-105796 | 4/2006 |
| JP | 2006-234693 | 9/2006 |

OTHER PUBLICATIONS

Japanese Office Action for Japanese Application No. 2008-506176 mailed on Jul. 10, 2012.

International Search Report for PCT/JP2007/000246 dated Apr. 17, 2007.

Murtz, Breath Diagnostics Using Laser Spectroscopy, Optics & Photonics News, vol. 16, No. 1, pp. 30-35, 2005.

* cited by examiner (a)

(b)

(a)

(b)

(a)

(b)

1001

ANALYZING ELEMENT AND ANALYZING APPARATUS USING SAME

TECHNICAL FIELD

The present invention relates to an analyzing element which analyzes a gas or liquid sample and an analyzing apparatus using the analyzing element.

BACKGROUND ART

Recently, as the progress of medical researches, a health diagnosis method which focuses on constituents contained in human breath has been established. For example, with respect to a visceral disease, an expiratory air analyzing diagnosis researches for determining which gas constituents exist according to kinds of visceral disease has been developed. Unlike a blood test for a patient (person under test) by using a syringe or the like, the expiratory air analysis does not cause a physical stress to a patient (person under test) and can collect sample easily. For example, a method of analyzing pylori in stomach by using a mass spectrometer has been commercially used as a medical diagnosis technique. According to recent researches, the expiratory air is known to contain much health information. Therefore, the expiratory air analysis is expected to prevail and progress greatly.

In addition, a technique for analyzing infinitesimal liquid constituents contained in blood or the like is expected to progress. Such a technique is not limited to biologic samples. For example, a technique for measuring infinitesimal gas constituents contained in an atmospheric air has been actively developed.

[Patent Document 1] Japanese Laid-open Patent Publication No. 2005-300212

[Patent Document 2] Japanese Laid-open Patent Publication No. H6-281568

[Non-patent Document 1] Manfred Murtz, Optics & Photonics News, vol. 16, No. 1, pp. 30-35 (2005)

DISCLOSURE OF THE INVENTION

Problems to be Solved by the Invention

The expiratory air analysis method using a commercialized mass spectrometer requires a considerable time for collecting an expiratory air or analyzing the expiratory air. The expiratory air analysis method is not such a method that can perform measurement and diagnosis on the spot immediately. However, recently, Non-Patent Document 1 discloses a technique capable of performing on-line measurement of an expiratory air in real-time by using an IR transmission absorption spectroscopy. In the IR transmission absorption spectroscopy, IR absorption occurs in infinitesimal gas constituents contained in the expiratory air, and transmission and absorption of the absorbed wavelength light of the tested infinitesimal gas constituents are measured. According to the method, even in case of an infinitesimal gas having an order of ppb to ppm, kinds and absolute amounts of the gas constituents can be measured instantaneously.

However, the current technical level of the IR absorption measurement method is merely a laboratory level. As well as optics including a laser source constructed with optical parts, a so-called "gas cell" which generally has a length of several tens of centimeters (in the aforementioned Non-Patent Document 1, 50 cm) and contains a gas under test for IR absorption are installed on a laboratory table. Therefore, there is a problem in that the associated measurement facility has no portability for easily carrying in medical sites.

Therefore, a problem solved by the present invention relates to a shape of an on-line measurement type expiratory air analysis system and, particularly, a size of the gas cell that have been difficult to carry.

In addition, the present invention has an intend to use the transmission absorption spectroscopy for an infinitesimal gas or liquid sample as a principle. Although a different spectroscopy, that is, a total reflection absorption spectroscopy (attenuated total reflection (ATR) method) is used, Patent Document 1 discloses a method of implementing a small size by using a light waveguide as a detection part for the aforementioned total reflection absorption spectroscopy.

In Patent Document 1, a device under test (DUT) is coated instead of an upper clad region of the light waveguide. The DUT is operated as a portion of the light waveguide by using a refractive index of the DUT, and thus, light distributed over the DUT is absorbed. As a result, the total reflection absorption spectroscopy can be performed.

The method is effective to a material that has some refractive index and can be coated. However, in case of an infinitesimal gas that is an object of measurement in the present invention, non-uniformity occurs in a layer-directional light distribution, and light can be easily radiated from a substrate. Therefore, there is a problem in that a stable state of propagation cannot be easily formed in terms of structure. In addition, taking into consideration a process for forming an actual light waveguide, a core layer is directly exposed from a surface thereof. Therefore, even though the process is easily adapted to a manufacturing process, there is a problem in that a large loss of waveguide occurs due to minute scratches or the like, which is assumed to be adapted easily to a manufacturing process.

The Patent Document 2 discloses a liquid constituent analyzing apparatus using a total reflection absorption spectroscopy (ATR method). As shown in FIG. 1 of the Patent Document 2, in the analyzing apparatus, a detection light is input from a side surface of a detection light waveguide and propagates through an inner portion of a light waveguide in a total reflection manner. However, in the method, since the evanescent light is absorbed only at positions on a boundary surface of the light waveguide where the light is totally reflected, it is difficult to obtain a sufficient measurement sensitivity. In addition, since an input angle is very limited, there is a problem in that it is difficult to determine an input angle and an output angle of light. In addition, the total reflection absorption spectroscopy (ATR method) disclosed in Patent Document 2 has the following problems.

(1) Since only one side of the light waveguide is used, an absorption amount is low.

(2) Since a total reflection angle is greatly changed according to an refractive index of a sample, light is designed to be input at a slanted angle by using reflection of IR light emitting diode (LED). Therefore, in some samples, the condition of total reflection may not be obtained.

(3) A result of measurement can be easily influenced by a change in an effective refractive index of a sample. Therefore, unless the sample is uniformly drawn to a sample chamber with an equal thickness thereof, an excessive loss (scattering loss or the like) occurs, so that it is not suitable for a highly-sensitive measurement.

For these reasons, the conventional example using the light waveguide cannot provide a light waveguide structure that is capable of being used as a sample cell and suitable to detect an infinitesimal gas or liquid.

The present invention is to implement an analyzing element and analyzing apparatus having a small size and being capable of measuring a gas or liquid constituent with a high accuracy.

Means of Solving the Problems

According to the present invention, there is provided an analyzing element including: a sample chamber into which a gas or liquid sample is introduced; a detection light waveguide arranged adjacent to the sample chamber for guiding detection light for detecting a sample; and a detection light inputting section for inputting the detection light, which is traveling in a direction along the detection light waveguides, into the detection light waveguides from the end surface of the detection light waveguides, wherein the detection light waveguide including an exposed surface exposed in the sample chamber.

In a conventional method where the detection light is transmitted through the sample cell, the cell needs to have a hollow structure so as to contain the sample. Since the detection light is transmitted through the hollow portion, it was difficult to change a direction of the waveguide.

On the contrary, the analyzing element according to the present invention has a structure where the light waveguides through which the detection light propagates and the cell containing the sample are separated from each other. When a sample exists in the cell, evanescent light leaking out from the light waveguides is absorbed, so that the light intensity of the light propagating through the light waveguides is decreased. From a result of measurement of a decrease in the light intensity, the sample may be qualitatively and quantitatively analyzed.

Since the present invention employs such an analysis method, it is possible to implement a small-sized analyzing element and to accurately measure a sample consisting of a gas, a liquid or a mixture thereof.

In addition, since the light waveguide may be constructed with, for example, a semiconductor stack structure, a polymer, an inorganic material, or the like, it is possible to arbitrarily change a direction of the waveguide by using a construction connected with a curved light waveguide. Therefore, the waveguide may be integrated with in a limited region with a high density, so that it is possible to ensure a long optical path length.

In addition, in the element according to the present invention, since the detection light is designed to be input from the end surface of the detection light waveguide and to propagate in a direction along the detection light waveguide, sufficient measurement sensitivity may be implemented. In a conventional total reflection absorption spectroscopy (attenuated total reflection (ATR) method), the detection light is input from a side surface of the detection light waveguide and propagate through an inner portion of the light waveguide in a total reflection manner. In this method, since the evanescent light is absorbed only at positions on a boundary surface of the light waveguide where the light is totally reflected, it is difficult to obtain a sufficient measurement sensitivity. In addition, since an input angle is very limited, there is a problem in that it is difficult to determine an input angle and an output angle of light. According to the present invention, the problems are solved, so that sufficient measurement accuracy may be obtained.

For example, the detection light waveguide may be disposed to extend in a predetermined direction. In addition, the exposed surface may be formed in a shape of band which surrounds the detection light waveguide.

In the present invention, the detection light waveguide may include first and second detection light waveguides which are disposed in parallel to each other with the sample chamber interposed therebetween, and the sample chamber may be disposed between the first and second detection light waveguides. By doing so, the light intensity distributed in the sample chamber is increased, so that it is possible to performing analysis with a higher accuracy. In this case, preferably, each of the exposed surfaces of the first and second detection light waveguides may be disposed to face each other with the sample chamber interposed therebetween. In addition, if a sum of widths of the first and second detection light waveguides is expressed by D, an interval between the first and second detection light waveguides may be, preferably, D or less, more preferably, D/2 or less. By doing so, it is possible to further increase a light intensity distribution in the sample chamber. Here, although the first and second detection light waveguides may have a shape of a straight line or a curve, it is preferable that the first and second detection light waveguides are disposed in parallel to each other with a predetermined separation distance. More preferably, the first and second detection light waveguides have a shape of a straight line and are disposed in parallel to each other.

According to the present invention, the analyzing element may have a light waveguide structure including: a substrate; and a mesa which is constructed with multiple layers of a lower clad layer, a core layer, and an upper clad layer which are stacked on the substrate in this order, wherein the core layer becomes the detection light waveguide, and a space adjacent to the mesa constitutes the sample chamber, and wherein a side surface of the core layer is exposed to an inner portion of the sample chamber.

According to the present invention, there is provided an analyzing element including: a detection light inputting section to which a detection light is input; an optical divider which divides the input detection light; a detector to which the divided detection light is guided; an optical coupler which couples the detection light output from the detector; and a detection light outputting portion which outputs the coupled detection light, wherein the detector has a sample chamber into which a gas or liquid sample is introduced and first and second detection light waveguides which are disposed in parallel to each other with the sample chamber interposed therebetween, wherein each of the first and second detection light waveguides has an exposed surface which is exposed to an inner portion of the sample chamber, and wherein the detection light propagating in a direction along the detection light waveguides is input to the detection light inputting portion.

The analyzing element may further have a light waveguide structure including: a substrate; and first and second mesas, each of which is constructed with multiple layers of a lower clad layer, a core layer, and an upper clad layer which are stacked on the substrate in this order, wherein the first and second mesas are disposed in parallel to each other, wherein the core layers of the first and second mesas become the first and second detection light waveguides, and a space interposed between the first and second mesas constitutes the sample chamber, and wherein a side surface of each of the core layers is exposed to the inner portion of the sample chamber.

The analyzing element may have first and second units, each of which is constructed with the detector, the optical divider, and the optical coupler, wherein the first and second units are optically connected with each other, and wherein the detection light waveguide included in the first unit and the detection light waveguide included in the second unit have different light-guide directions.

In this case, the first and second units may be connected with each other through a curved light waveguide. In addition, both of the detection light waveguides included in the first and second units may have a shape of straight line and are disposed in parallel to each other. In addition, each of the first and second units may have first and second detection light waveguides which are disposed in parallel to each other with the sample chamber interposed therebetween.

In the present invention, the detection light inputting portion and the detection light outputting portion may have a mirror, and each of the mirrors may be constructed so as to reflect a portion of the detection light and to transmit other portions thereof. By doing so, it is possible to perform analysis with a higher accuracy. In addition, a quantitative analysis can be performed based on an attenuation rate of the output light.

According to the present invention, there is provided an analyzing apparatus having a light source, an analyzer to which a light is input from the light source, and a photodetector which detects a light output from the analyzer, wherein the analyzer has the aforementioned analyzing element, and wherein the sample is analyzed based on a relationship between an intensity of the light input to the analyzer of the analyzing element and an intensity of the light output from the analyzer.

In the present invention, the analyzer may further comprise an expiratory air collector which collects an expiratory air and draws the expiratory air into the sample chamber. By doing so, it is possible to implement an analyzing element capable of speedily and accurately analyze the expiratory air.

According to the present invention, there are provided analyzing elements, analyzing apparatuses, and systems having the following constructions.

(A) An analyzing element constructed with a light waveguide type cell having a structure where an input-light waveguide, an optical coupling/dividing waveguide, a gas-detection light waveguide, a curved light waveguide, and an output-light waveguide are integrated on a substrate.

(B) The analyzing element according to (A), wherein the gas-detection light waveguide has a light waveguide structure where a first clad layer, a core layer, and a second clad layer are stacked on the substrate, wherein the core layer is disposed at a position spatially higher than a bottom of the substrate, and wherein the light waveguide type cell has a structure where a plurality of the gas-detection light waveguides are aligned to be adjacent to each other.

(C) The analyzing element according to (B), wherein both of end surfaces of the input-light waveguide and the output-light waveguide are formed with high-reflectivity mirrors.

(D) An analyzing element constructed with a light waveguide type cell having a structure where an input-light waveguide, an optical amplifier, an optical coupling/dividing waveguide, a gas-detection light waveguide, a curved light waveguide, and an output-light waveguide are integrated on a substrate.

(E) The analyzing element according to (D), wherein the gas-detection light waveguide has a light waveguide structure where a first clad layer, a core layer, and a second clad layer are stacked on the substrate, wherein the core layer is disposed at a position spatially higher than a bottom of the substrate, and wherein the light waveguide type cell has a structure where a plurality of the gas-detection light waveguides are aligned to be adjacent to each other.

(F) The analyzing element according to (E), wherein both of end surfaces of the input-light waveguide and the output-light waveguide are high-reflectivity mirrors.

(G) A gas analyzing apparatus having the analyzing element according to (A) to (F) as a gas cell.

(H) A expiratory air analyzing apparatus having the analyzing element according to (A) to (F) as a gas cell.

(I) A gas analysis system, in which the gas analyzing apparatus according to the (G) is connected to a computer, thereby analyzing gas constituent data obtained by the gas analyzing apparatus.

(J) A gas analysis system, in which the gas analyzing apparatus according to the (G) and a computer are connected to a network, thereby performing an analysis based on gas constituent data obtained by the gas analyzing apparatus.

(K) The gas analysis system according to the (I), which is implemented in a mobile phone.

(L) A expiratory air analysis diagnosis system, in which the expiratory air analyzing apparatus according to the (H) is connected to a computer, thereby performing a health diagnosis based on expiratory air constituent data analyzed by the expiratory air analyzing apparatus.

(M) A expiratory air analysis diagnosis system, in which the expiratory air analyzing apparatus according to the (H) and a computer are connected to a network, thereby performing a health diagnosis based on expiratory air constituent data analyzed by the expiratory air analyzing apparatus.

(N) The expiratory air analysis diagnosis system according to the (M), which is implemented in a mobile phone.

Hereinafter, operations of the inventions according to the (A) to (N) will be described.

In the (A) to (N), the light waveguide type cell is operated as a light waveguide. On the other hand, the cell is actively operated so as to distribute light in the gas phase. In addition, an external infinitesimal gag can be easily introduced.

A general gas cell used for light transmission absorption spectroscopy for an infinitesimal gas is a part having a shape of a cylinder (length: about several tens of centimeters, a radius: about several tens of centimeters). A sealed space is filled with the gas under test, and light is allowed to propagate through the space. In general, since a light propagates straight, in order to generate light absorption effective to measurement, such a large size is required. If the light waveguide propagation may be used instead of a spatial propagation, the same optical path length may be received within a size of about several millimeters to several centimeters. However, since the light waveguide propagation is generally performed along a sold state material, the infinitesimal gas under test is not contained in the light waveguide in terms of construction. In addition, a hollow waveguide where a space is surrounded by a total reflection mirror may be considered. However, since a sealed structure (a structure isolated from an external space) is surrounded by the total reflection mirror, it is physically difficult to introduce an infinitesimal gas from an external site in terms of structure. In addition, since it is difficult to dispose a reflection mirror having a 100% reflectance in an inner portion of the hollow waveguide, the hollow waveguide basically should have a large waveguide loss. The hollow waveguide is not suitable for propagation of several tens of centimeters or more in terms of structure.

The light waveguide type cell according to the (A) to (N) is constructed with light waveguides and operated to actively distribute light in the gas phase. Unlike the hollow waveguide, since the cell has no sealed structure, as described above, the cell is operated as a light waveguide to actively distribute the light in the gas phase and in addition, the cell easily is introduced an infinitesimal gas from an external site.

Effects of the Invention

According to the present invention, an analyzing element and an analyzing apparatus having a small size and being capable of measuring a gas constituent or a liquid constituent with a high accuracy can be provided.

BRIEF DESCRIPTION OF THE DRAWINGS

The above and other objects, advantages, and features will be more apparent from the following description of certain preferred embodiments taken in conjunction with the accompanying drawings.

BEST MODE FOR CARRYING OUT THE INVENTION

The invention will be now described hereinafter with reference to preferred embodiments.

(First Embodiment)

A first embodiment will be described in detail with reference to the drawings.

Figure 1:
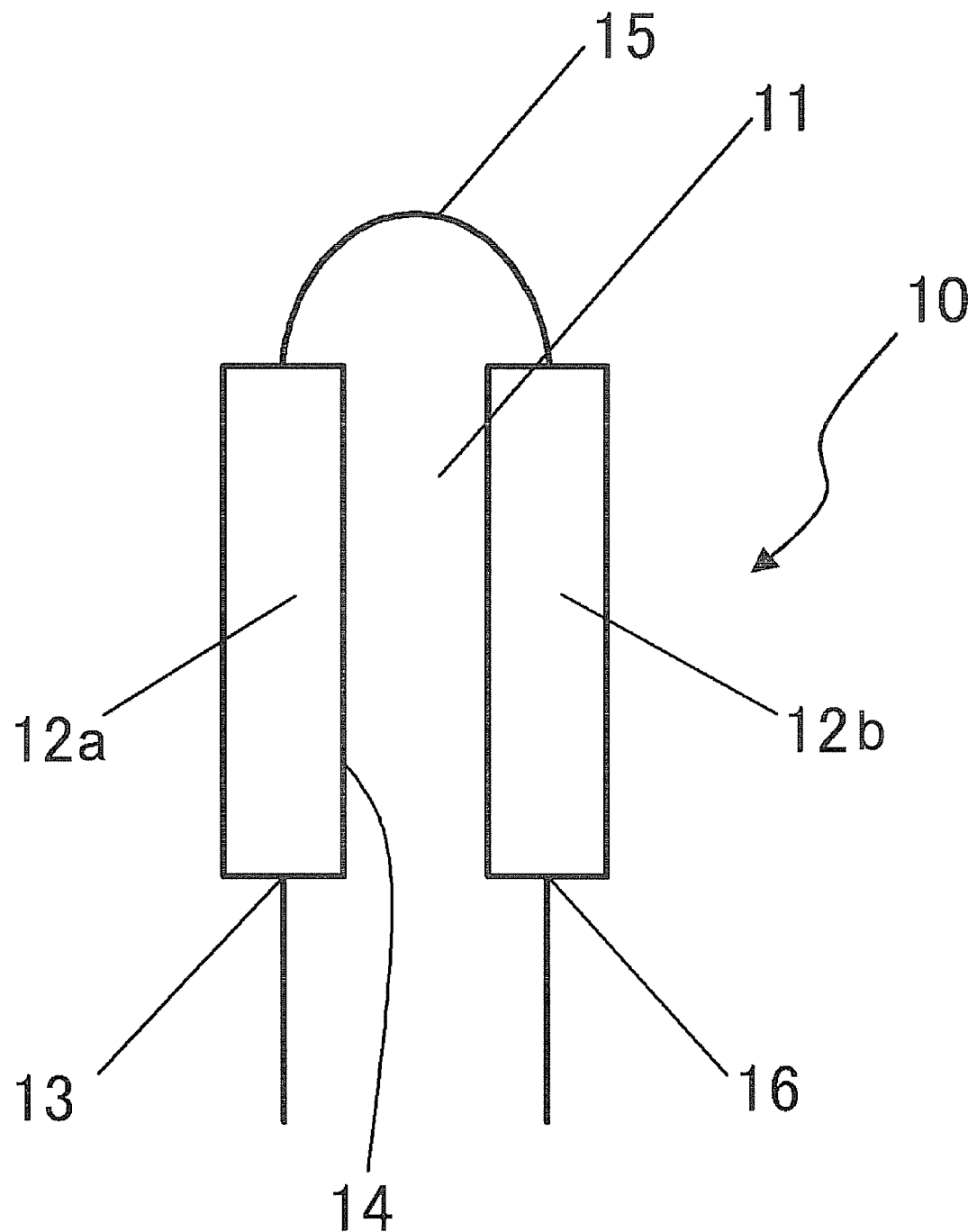
FIG. 1 is a view showing a first embodiment.

FIG. 1 schematically shows a construction of an analyzing element 10 according to the embodiment.

The analyzing element 10 includes a sample chamber 11 into which a gas sample is introduced, detection light waveguides 12a and 12b arranged adjacent to the sample chamber 11 for guiding detection light for detecting a sample, and a detection light inputting section 13 to which the detection light propagating through the detection light waveguide 12a and 12b in a direction along the detection light waveguides 12a and 12b is input from end surfaces of the detection light waveguides 12a and 12b. Each of the detection light waveguides 12a and 12b has an exposed surface 14 which is exposed to the sample chamber 11.

The detection light which is input from the detection light inputting portion 13 to the detection light waveguide 12a propagates through the detection light waveguides 12a and 12b to be output from a detection light outputting portion 16. A curved waveguide portion 15 connects the detection light inputting portion 13 and the detection light outputting portion 16. The curved waveguide portion 15 may be use, for example, an optical fiber.

In the embodiment, the detection light is input from the end surfaces of the detection light waveguides 12a and 12b and propagates in the direction along the detection light waveguides 12a and 12b. Since the sample is a gas, the sample can absorb the light along the entire length of the detection light waveguide.

Each of the detection light waveguides 12a and 12b has a shape of straight line extending in a predetermined direction, so that the detection light waveguides are disposed to be parallel to each other.

The detection light waveguides 12a and 12b are disposed to be in parallel to each other with the sample chamber 11 interposed therebetween. That is, the sample chamber 11 is disposed between the detection light waveguide 12a and the detection light waveguide 12b.

In addition, in the analyzing element 10, the exposed surfaces 14 of the detection light waveguides 12a and 12b are disposed to face each other with the sample chamber 11 interposed therebetween.

Each of the detection light waveguides 12a and 12b has the exposed surface 14 which is exposed to the sample chamber 11. The exposed surface 14 is provided in a shape of band which surrounds each of the detection light waveguide. Sidewalls of the detection light waveguides 12a and 12b become the wall of the sample chamber 11.

Therefore, the sample chamber 11 denotes a space which is interposed between the side walls of the detection light waveguides 12a and 12b, so that the sample chamber is partitioned by the side walls.

When the light is guided by the detection light waveguides 12a and 12b, a portion of the light propagating through the detection light waveguides 12a and 12b is leaked out from the exposed surfaces 14, so that predetermined lights are distributed in the sample chamber. The gas introduced into the sample chamber 11 absorbs the leaking lights. In proportion to a degree of light absorption of the gas in the sample chamber 11, an intensity of the light propagating through the detection light waveguides is decreased. From a result of measurement of a decrease in the light intensity, the sample can be analyzed.

The sample chamber 11 is a sample introducing region which has a function as a gas cell. The sample chamber 11 is also a region which holds the sample. In the region, the sample may be flown or stopped.

Hereinafter, an example of a gas light-absorption analyzing method using the analyzing element 10 according to the embodiment will be described.

A gas of which absorption coefficient is known is introduced into the sample chamber 11, and a light having a predetermined light intensity is input from the detection light inputting portion 13 thereto in advance. The light propagates through the detection light waveguides 12a and 12b to be output from the detection light outputting portion 16. The light intensity of the output light is detected by a photodetector. An absorbance of the gas is obtained from a relationship between the light intensity of the input light which is input to the detection light waveguides 12a and 12b and the light intensity of the output light which outputs from the detection light waveguides 12a and 12b, so that a concentration of the gas can be calculated.

Hereinafter, operations and effects of the embodiment will be described.

According to the analyzing element of the embodiment, since the detection light waveguide through which the detection light propagates and the sample cell are separated from each other, a degree of freedom in planar layout of the light waveguides can be improved, so that it is possible to ensure a long optical path length. Therefore, by using the analyzing element according to the present invention, it is possible to implement a small-sized analyzing apparatus and to accurately measure an infinitesimal sample.

In the analyzing element according to the embodiment, since the detection light is guided by the light waveguide, optical loss can be reduced in comparison with a conventional gas cell method.

In the conventional method where the detection light is transmitted through the sample cell, the cell needs to have a hollow structure so as to contain the sample. Since the detection light is transmitted through the hollow portion, it was difficult to change a direction of the waveguide.

On the contrary, the analyzing element according to the present invention has a structure where the light waveguides through which the detection light propagates and the cell containing the sample are separated from each other. When a sample exists in the cell, evanescent light leaking out from the light waveguides is absorbed, so that the light intensity of the light propagating through the light waveguides is decreased. From a result of measurement of a decrease in the light intensity, the sample can be qualitatively and quantitatively analyzed.

Since the present invention employs such an analysis method, it is possible to implement a small-sized analyzing element and to accurately measure a sample consisting of a gas, a liquid or a mixture thereof.

In addition, since the light waveguide can be constructed with, for example, a semiconductor stack structure, a polymer, an inorganic material, or the like, it is possible to arbitrarily change a direction of the waveguide by using a construction connected with a curved light waveguide. Therefore, the waveguide can be integrated with in a limited region with a high density, so that it is possible to ensure a long optical path length.

Next, another embodiment of the present invention will be described. In the following description, an analyzing element is suitably referred to as a "light waveguide type cell."

(Second Embodiment)

Now, a second embodiment will be described in detail with reference to FIG. 2.

A light waveguide type cell 801 includes an input-light waveguide 101 to which a detection light is input, an optical coupling/dividing waveguide 102 which divides the input detection light, a gas-detection light waveguide 103 which guides the divided detection lights, an optical coupling/dividing waveguide 102 which couples the detection lights output from the gas-detection light waveguide 103, and an output-light waveguide 105 which outputs the coupled detection light. The gas-detection waveguide 103 is constructed with a sample chamber 11 into which a gas is introduced and two detection light waveguides which are disposed to be parallel to each other with the sample chamber 11 interposed therebetween. Each of the detection light waveguides has an exposed surface which is exposed to the sample chamber 11. The input-light waveguide 101 is constructed so that the detection light which propagates through the detection light waveguide is input thereto.

Here, a construction for dividing and coupling the detection lights may be made in various manners. FIG. 2 shows an example thereof. A optical coupling/dividing waveguide 102 shown in FIG. 2(a) represents a 1×2 MMI coupler structure. A optical coupling/dividing waveguide 102 shown in FIG. 2(b) represents a Y-branched structure. In the embodiment, the optical coupling/dividing waveguide 102 may have any structure, provided that the optical coupling/dividing waveguide has functions of dividing the input detection light and coupling the detection lights output from the gas-detection light waveguide 103.

Figure 2:
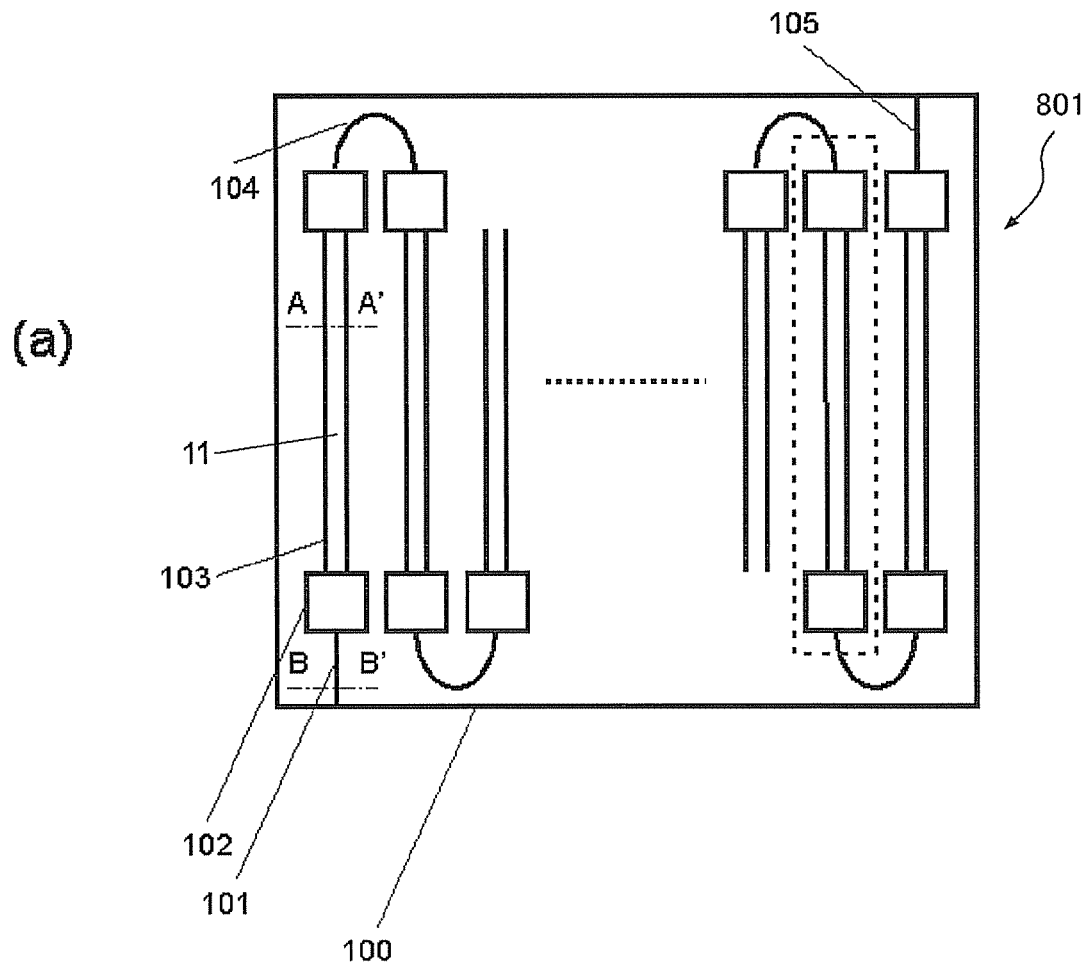
FIG. 2 is a schematic view showing a construction of a second embodiment, and (b) is an extended view of (a).
Figure 2:
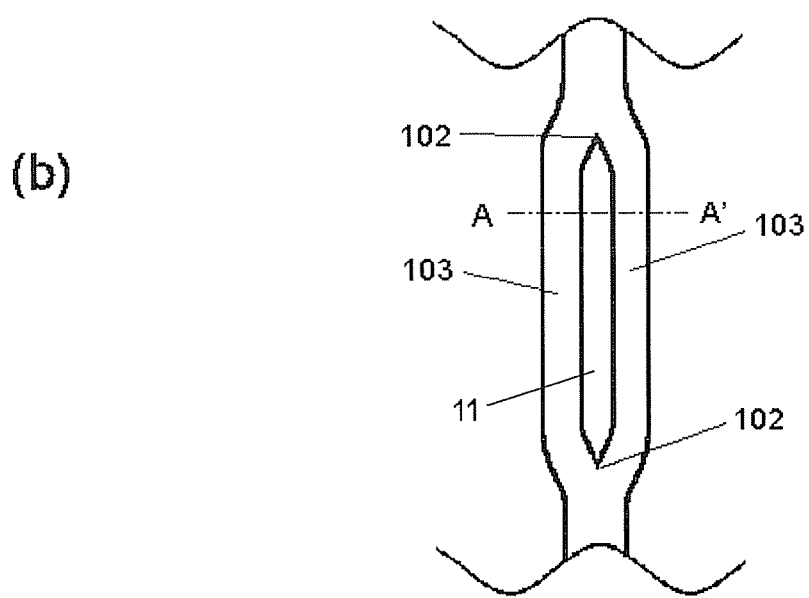
Figure 3:
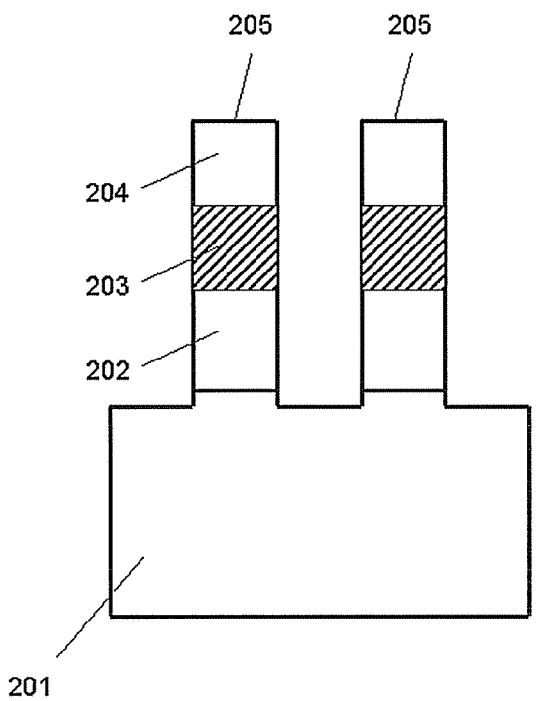
FIG. 3 is a schematic cross-sectional view showing a structure of a gas-detection light waveguide used in the second embodiment.

FIG. 3 is a view showing a cross-sectional structure of the gas-detection light waveguide 103 taken along line A-A' of FIG. 2.

The light waveguide type cell 801 has a light waveguide structure including two high mesas 205, each of which has an Si substrate 201 and multiple layers of a first $SiO_2$ clad layer 202, an Si core layer 203, and a second $SiO_2$ clad layer 204 which are stacked on the Si substrate 201 in this order. The two high mesas 205 are disposed to be parallel to each other. The Si core layers 203 become the detection light waveguides, respectively, and a space interposed between the two high mesas 205 becomes the sample chamber 11. The side surfaces of the Si core layers 203 are exposed to the sample chamber 11.

Returning to FIG. 2, the light waveguide type cell 801 will be described in detail. The light waveguide type cell 801 includes a plurality of units, each of which has the gas-detection waveguide 103 and the two optical coupling/dividing waveguides 102. The units are optically connected to each other. The detection light waveguides included in adjacent units have different light-guide directions, respectively. The two detection light waveguides included in the unit have the same light-guide direction.

The units are connected with each other through the curved light waveguide 104.

In addition, the detection light waveguides included in each of the units have a shape of a straight line and are disposed in parallel to each other.

In addition, each of the units has the detection light waveguides which are disposed in parallel to each other with the sample chamber interposed therebetween.

In the embodiment, in addition to the region interposed between the parallel detection light waveguides, regions adjacent to outer sides of the detection light waveguides are operated as a sample chamber. In other words, in the regions adjacent to the outer sides of the detection light waveguides, light absorption of the sample occurs.

The light waveguide type cell 801 is formed by integrating the input-light waveguide 101, the optical coupling/dividing waveguides 102, the gas-detection light waveguides 103, the curved light waveguides 104, and the output-light waveguide 105 on the substrate 100. The input-light waveguide 101 and the output-light waveguide 105 have a waveguide width of about 0.9 μm and a length of about 100 μm. The optical coupling/dividing waveguide 102 has a waveguide width of about 4 μm and a length of about 25 μm. In addition, the gas-detection light waveguide 103 has a region length of about 1 cm.

Figure 4:
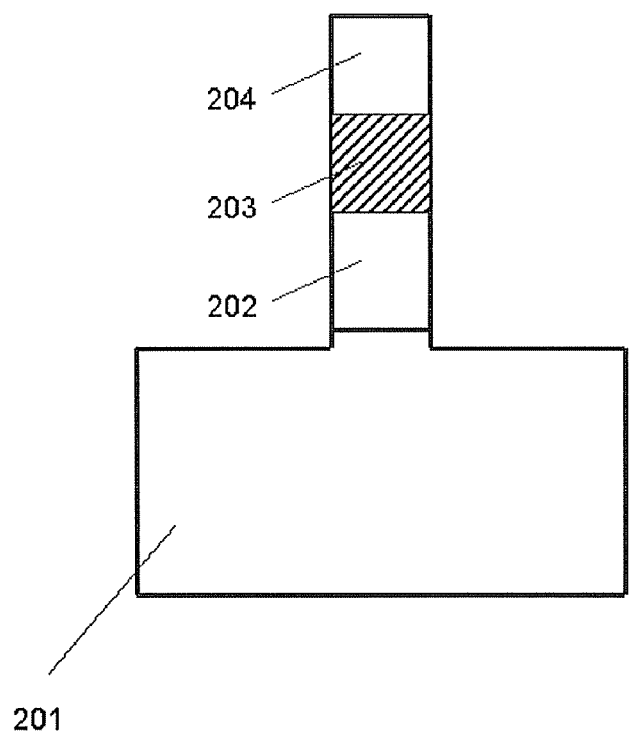
FIG. 4 is a schematic cross-sectional view showing structures of an input-light waveguide, an optical coupling/dividing waveguide, a curved light waveguide, and an output-light waveguide used in the second embodiment.

As shown in FIG. 3, in the cross-sectional structure of the gas-detection light waveguide 103 taken along line A-A' of FIG. 2, two high mesa light waveguides are close to each other with a waveguide interval of about 900 nm, and a light waveguide width thereof is about 900 nm. The curved light waveguide 104 has a curvature radius of about 5 µm. In addition, as sown in FIG. 4, the cross-sectional structures of the input-light waveguide 101, the optical coupling/dividing waveguide 102, and the curved light waveguide 104 taken along line B-B' of FIG. 2(a) are high mesa structures. The stacked structure of the light waveguide shown in FIGS. 3 and 4 is a high mesa structure 205 where the first $SiO_2$ clad layer 202, the Si core layer 203, and the second $SiO_2$ clad layer 204 are stacked o the Si substrate 201. The first $SiO_2$ clad layer 202 has a thickness of about 1 µm. The Si core layer 203 has a thickness of about 0.3 µm. The second $SiO_2$ clad layer 204 has a thickness of about 1 µm. A wavelength band in use is in the vicinity of a communication wavelength band (1.55 µm).

Figure 5:
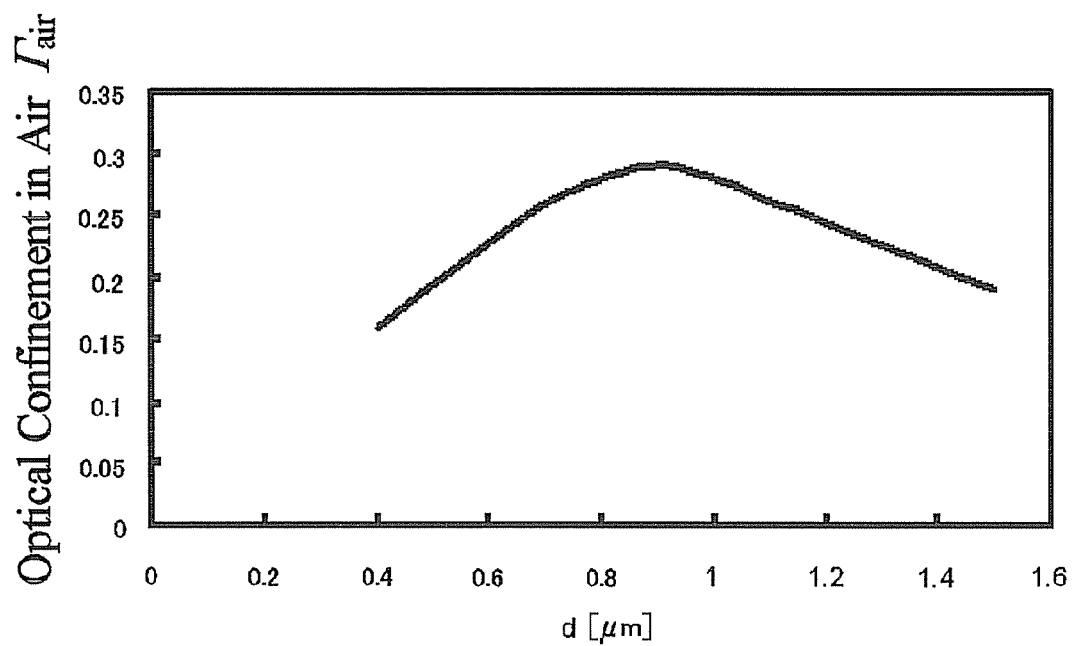
FIG. 5 is a view for explaining a principle of detection of a gas by using the gas-detection light waveguide according to the second embodiment.

Hereinafter, a principle of detection of infinitesimal gas constituents by using the light waveguide type cell according to the second embodiment of the present invention will be described. As shown in FIG. 3, the gas-detection light waveguide 103 of the light waveguide type cell according to the present invention is constructed with two adjacent high mesa light waveguides. In the light waveguide type cell according to the second embodiment, a structure where the two high mesa light waveguides are disposed to be close to each other is used as the gas-detection waveguide. For this reason, optical coupling occurs between the light waveguides, so that the light amount distributed in the gas phase is increased. FIG. 5 shows a result of a light distribution ratio $\Gamma_{air}$ in the air according to an interval d between the two high mesa light waveguides, which is obtained by using a three-dimensional beam propagation method. It can be seen that, when the interval d is about 900 nm, about 30% of the light is distributed in the gas phase.

If a width of each high mesa light waveguide is set to x and if an interval between the waveguides is set to d, from the result shown in FIG. 5, it can be understood that the following relation is preferable in terms of increasing the distribution of the light intensity in the gas phase.

$x/10 \le d \le 2x$

In addition, the following is more preferable.

$x/2 \le d \le 3x/2$

In addition, in the example shown in FIG. 5, the maximum distribution of the light intensity is obtained at the time of x=d.

In this manner, in the element according to the embodiment, since light having a predetermined light intensity is distributed in the gas phase, transmission, absorption, and spectroscopy are available for infinitesimal gas constituents. According to the embodiment, since a plurality of the gas-detection light waveguides 103 are integrated with the curved light waveguides 104, as a total optical path length of the gas-detection light waveguides 103, about 10 m within a size of about 1 cm can be implemented. Therefore, in comparison with a conventional gas cell, a small-sized cell having a long optical path length of 1 digit or more and a small element size of 1 digit or more can be implemented.

In the embodiment, although the two high mesas are disposed to be close to each other, the number of the high mesas may be two or more. For example, three high mesas or five high mesas may be used. In addition, in the embodiment, although the gas-detection light waveguide 103 has a shape of a straight line, the curved light waveguides 104 may be constructed as the gas-detection light waveguide where a plurality of high mesa waveguides are disposed to be close to each other. In this case, unnecessary optical coupling/dividing waveguides therebetween may be removed. In addition, although the curvature radius is set to 5 µm, the present invention is not limited thereto. For example, the curvature radius may be 25 µm or 500 µm. Furthermore, at the front stage of the input-light waveguide 101 or at the rear stage of the output-light waveguide 105, a spot size converter or a tapered light waveguide for improving connection efficiency with respect to an optical fiber may be inserted. In addition, although a length of the region of gas-detection light waveguides 103 is set to about 1 cm, the present invention is not limited thereto. The length may be set to be longer or shorter. For example, the length may be 3 cm or 1 mm. In addition, in the embodiment, a light waveguide structure where the input-light waveguide 101 and the output-light waveguide 105 are formed indifferent cross-sectional directions is used. However, the present invention is not limited thereto, but the input-light waveguide 101 and the output-light waveguide 105 may be formed in the same cross-sectional direction. Although the wavelength band in use is in the vicinity of a communication wavelength band (1.55 µm), the present invention is not limited thereto. For example, a visible light band or a mid-IR band may be used.

In addition, although the optical coupling/dividing waveguide 102 is constructed with a general 1×2 optical coupling/dividing waveguide, the present invention is not limited thereto. For example, the number of branches may be changed according to the number of high mesa light waveguides. In addition, the optical coupling/dividing waveguide 102 may be an optical coupling/dividing waveguide having a light distribution matching region.

Figure 11:
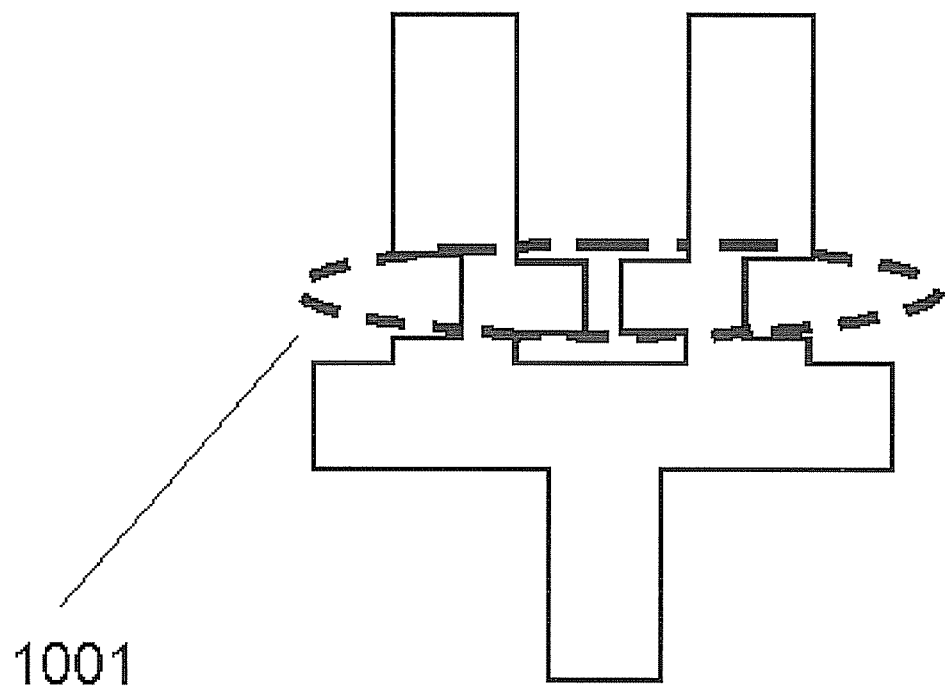
FIG. 11 is a view showing an example of an optical coupling/dividing waveguide according to the second, fourth, and sixth embodiments.

FIG. 11 is a view showing an example of the optical coupling/dividing waveguide 102. The optical coupling/dividing waveguide 102 is added with a light distribution matching region 1001. Hereinafter, a structure and functions of the optical coupling/dividing waveguide 102 will be described.

Figure 12:
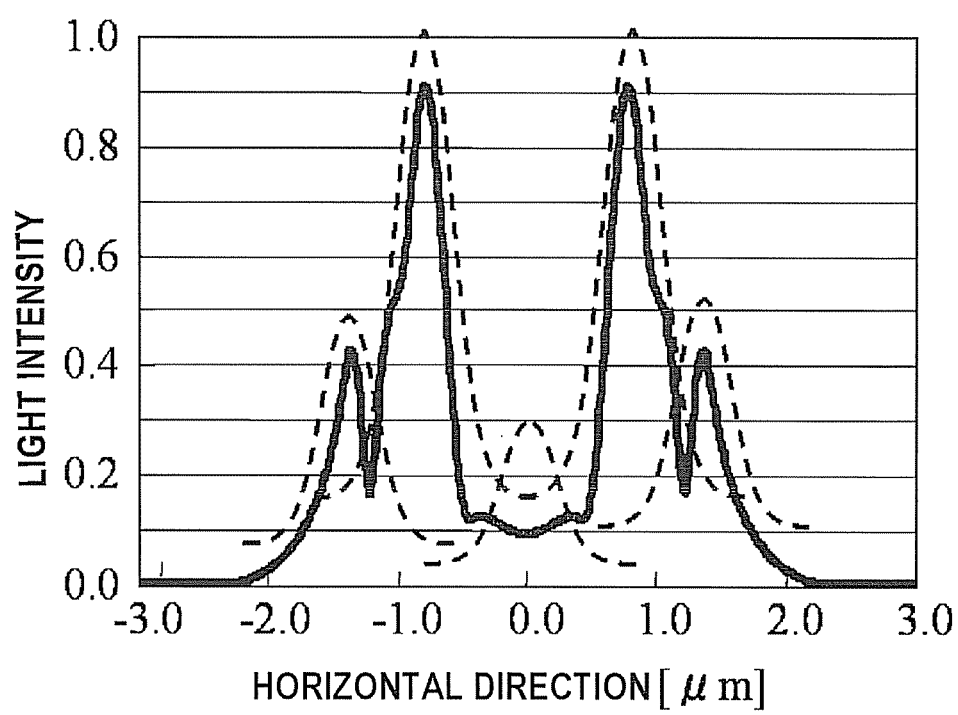
FIG. 12 is a view for explaining the optical coupling/dividing waveguide according to the second, fourth, and sixth embodiments.

FIG. 12 is a view showing a light field phase which can be obtained in case of a double high mesa structure. It can be understood from simulation that a high light intensity distribution can be obtained by forming the state of the light field shown in FIG. 12. As shown by a solid line of FIG. 12, it is assumed that two strong peaks exist in a light waveguide and tails of the left and right strong peaks and a central weak peak exist in a valley between light waves. In this case, the propagating light in the double high mesa structure can be substantially approximated to a superposition of about five Gaussian beams. The optical coupling/dividing waveguide 102 shown in FIG. 11 is designed to be in the state of superposition of the five Gaussian beams.

The optical coupling/dividing waveguide 102 can represent initial four peaks by adding two light waveguides at inward positions which are separated by short distances from the left and right general high mesa light waveguides in a horizontal direction. In addition, with respect to the central weak peak, an MMI region length is designed to be slightly shorter or longer than a theoretical optimal value. Therefore, at positions where the light is originally coupled with only the left and right light waveguides, an effect that some portion of light may occur even at the central portion can be used. Accordingly, due to the optical coupling/dividing waveguide 102, the state of superposition of the five Gaussian beams can be formed. In addition, due to the addition of the light distribution matching region 1001 to the optical coupling/dividing waveguide 102, it is possible to suppress a loss of coupling in the propagating light.

Figure 6:
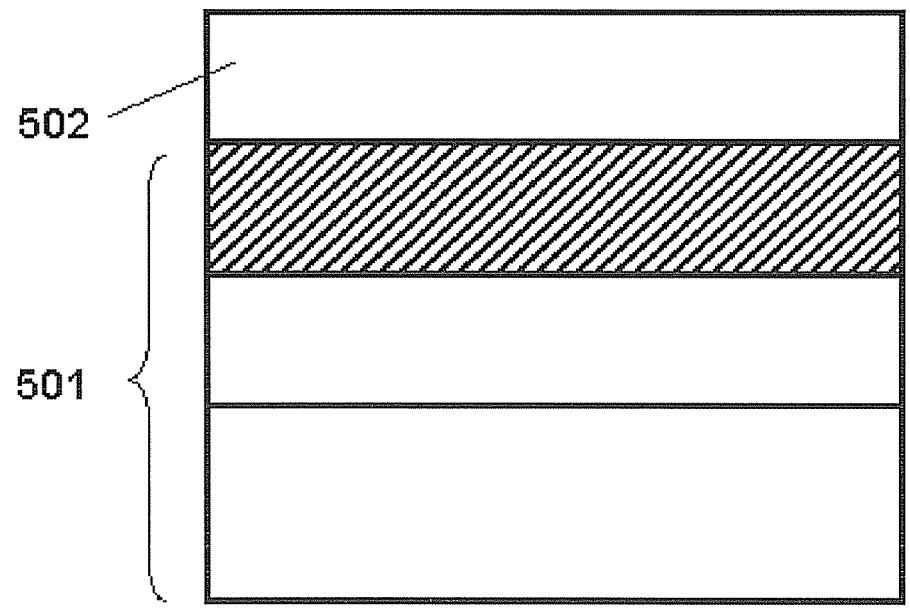
FIG. 6 is a cross-sectional view showing processes in methods of manufacturing light waveguide type cells according to the second, fourth, and sixth embodiments.
Figure 6:
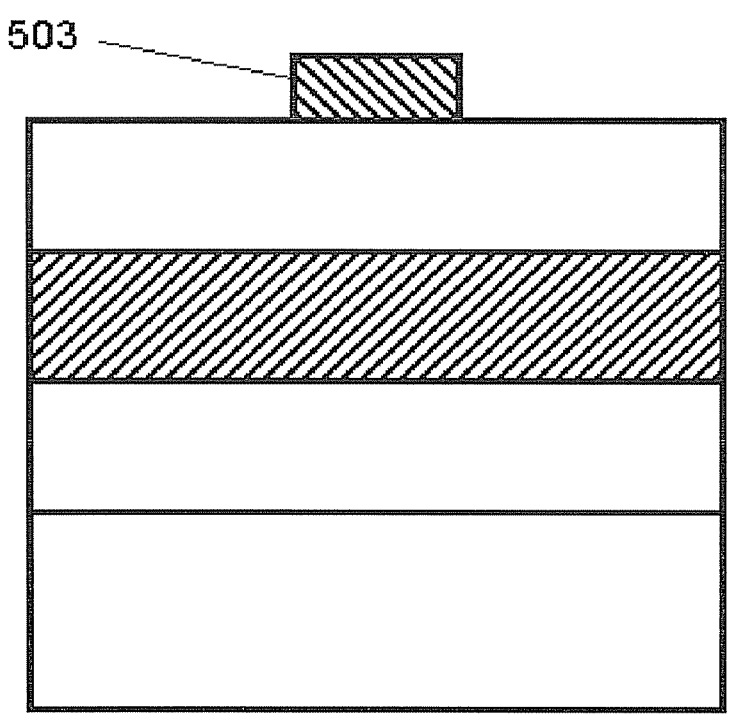
Figure 7:
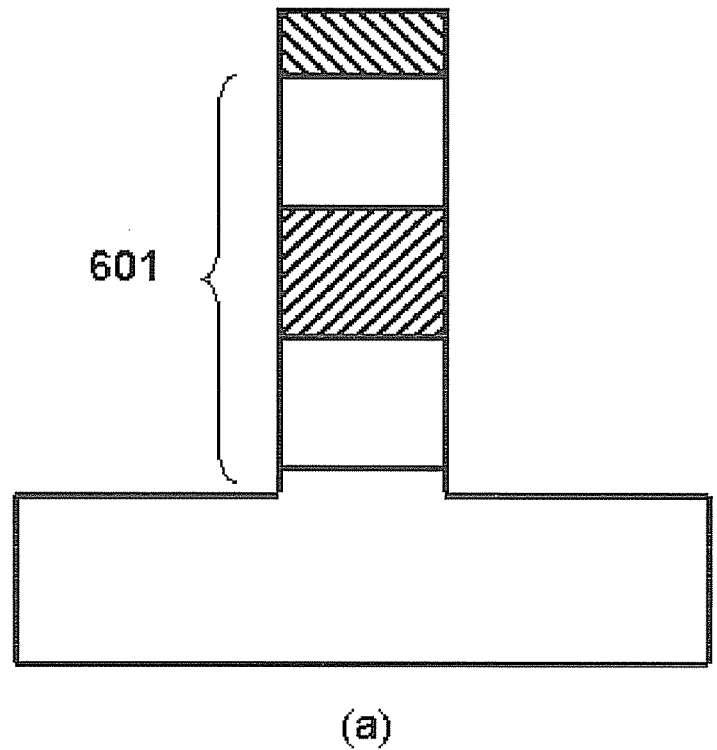
FIG. 7 is a cross-sectional view showing processes in methods of manufacturing light waveguide type cells according to the second, fourth, and sixth embodiments.
Figure 7:
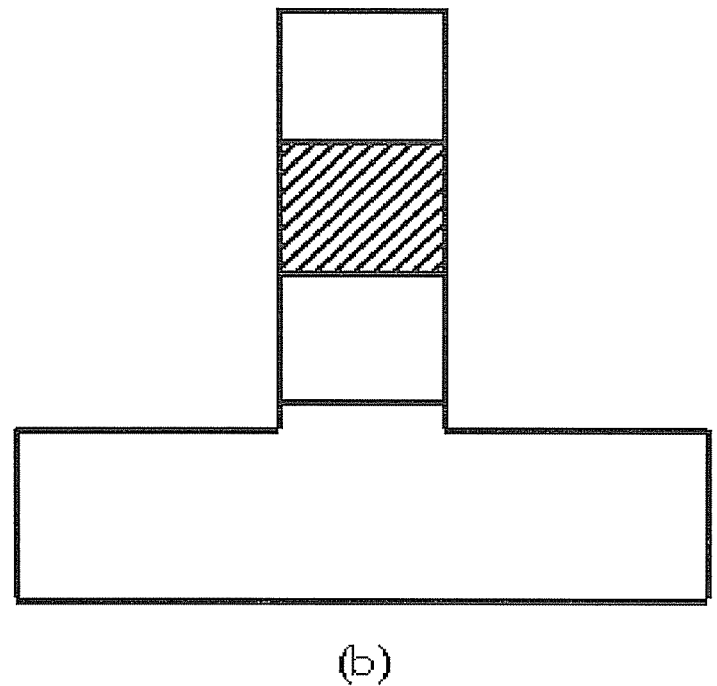

Hereinafter, a method of manufacturing the analyzing element including the high mesa structure will be described with reference to FIGS. 6 and 7.

Firstly, an $SiO_2$ film 502 is deposited on a general SOI substrate 501 by using a thermal CVD method (see FIG.

6(a)). Next, a mask 503 is formed in a shape of waveguide by using a photolithography method using a stepper (reduced-projection exposure) (see FIG. 6(b))). Etching is performed by using the mask through an inductively-coupled plasma (ICP) method to form a high mesa 601 (see FIG. 7(a)). Next, the mask 503 on the high mesa 601 is removed by using an organic solvent and an ashing method (see FIG. 7(b)). Next, the light waveguide type cell 801 is cut, and an end surface thereof is polished, and after that, that the method of manufacturing the element is completed.

In addition, in the embodiment, the stepper is used for the lithography. However, the present invention is not limited thereto. For example, an electron beam exposure may be used. In addition, although the thermal CVD is used as the method of forming the $SiO_2$ film 502, for example, a plasma CVD method or a sputtering method may be used. In addition, the method of forming the mesa is not limited to the ICP method, but, for example, an RIE method may be used. In addition, in the embodiment, the high mesa structure where etching is performed down to the Si substrate 201 is formed. However, the etching is not necessarily performed down to the Si substrate 201, but the etching may be performed down to the Si core layer 203. In addition, in the embodiment, the light waveguide structure where the SOI substrate 501 is used and the core layer and the clad layer are made of Si and $SiO_2$, respectively, is formed. However, the present invention is not limited thereto, but materials which basically constitute a light waveguide can be used. For example, the substrate, the clad layer, and the core layer may be made of Si, $SiO_2$, and SiN, respectively. In addition, the substrate may be made of a composite semiconductor InP, and the clad and the core layer may be made of InP and InGaAsP, respectively. In addition, polymer materials may be used. AS the matter of course, in the embodiment, after the cutting of the light waveguide type cell 801, the polishing is performed. However, a cleaving process may be performed.

(Third Embodiment)

A third embodiment will be described in detail with reference to the drawings.

Figure 8:
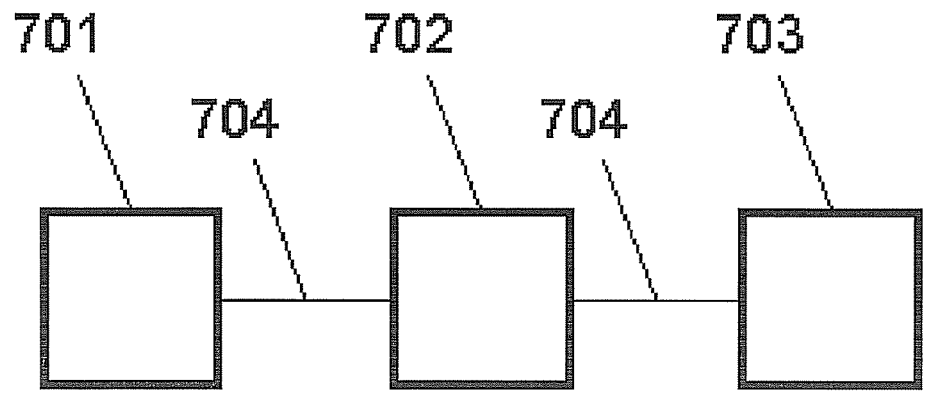
FIG. 8 is a schematic view showing constructions of the third, fifth, and seventh embodiments.

FIG. 8 schematically shows a construction of a gas analyzing apparatus as the third embodiment.

The gas analyzing apparatus includes a wavelength-variable light source 701, a light waveguide type gas cell 702 to which a light is input from the wavelength-variable light source 701, and a photo-detector 703 which detects a light output from the light waveguide type gas cell 702. The light waveguide type gas cell 702 has a light waveguide type cell 801 to perform analysis of a sample based on a relationship between an intensity of the light inputting to the light waveguide type gas cell 702 having the light waveguide type cell 801 and an intensity of the light output from the light waveguide type gas cell 702.

In the gas analyzing apparatus, the wavelength-variable light source 701, the light waveguide type gas cell 702, and the photo-detector 703 are connected to each other by optical fibers 704.

Figure 9:
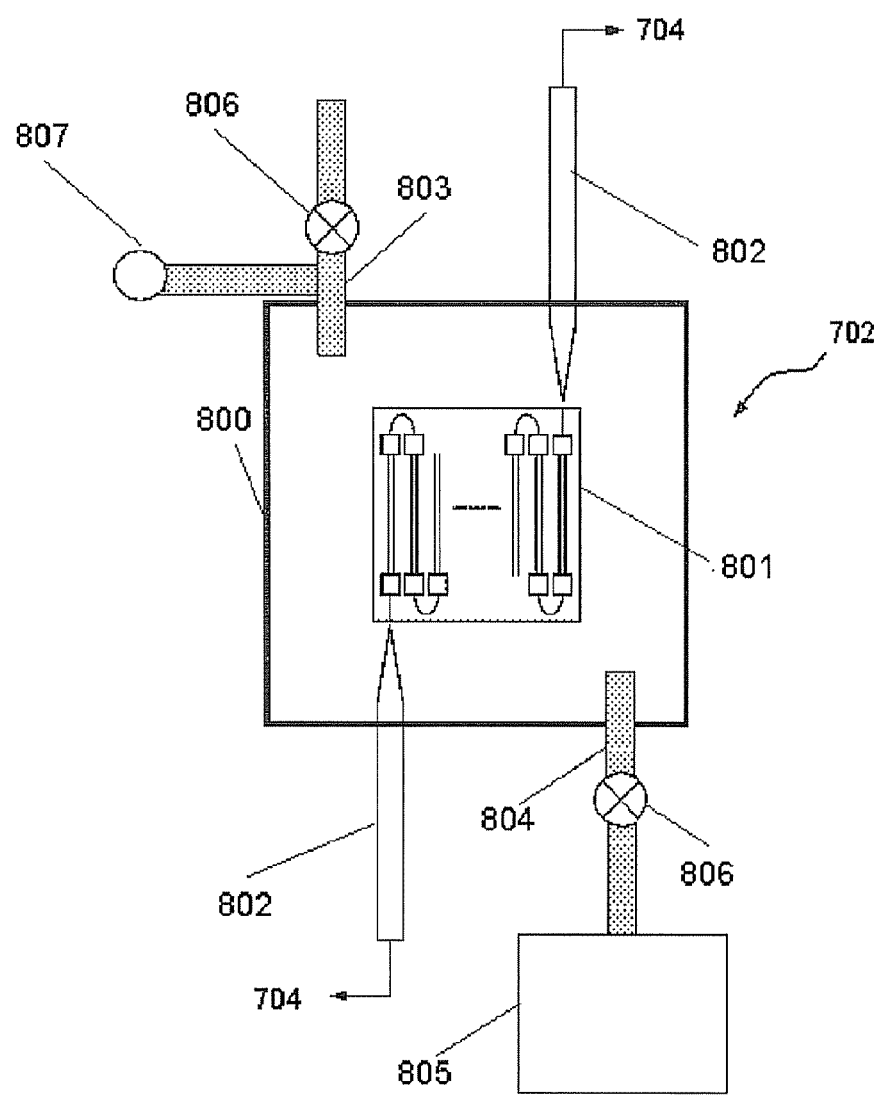
FIG. 9 is a schematic view showing constructions of light waveguide type gas cells used in the third, fifth, and seventh embodiments.

FIG. 9 schematically shows a construction of the light waveguide type gas cell 702. A light waveguide type cell 801, a front-stage optical fiber 802, a gas inlet port 803, and a gas outlet port 804 are disposed in a case 800. A gas sample is introduced into an inner portion of the case 800. A vacuum pump 805 is connected to the gas outlet port 804 to lead the to-be-measured infinitesimal gas introduced from the gas inlet port 803 into the inner portion of the case 800. In addition, a stop valve 806 and a pressure gauge 807 are provided to control a pressure of the inner portion of the case 800.

The light waveguide type cell 801 is contained in the case 800. The structure thereof is equivalent to that of the light waveguide type cell described in the second embodiment.

In the embodiment, since all the case 800 is operated as a gas cell, the gas sample is introduced around the detection light waveguides disposed therein. Therefore, in addition to the region interposed between the parallel detection light waveguides, regions adjacent to outer sides of the detection light waveguides are operated as a sample chamber. In other words, in the regions adjacent to the outer sides of the detection light waveguides, light absorption of the sample occurs.

In addition, in the embodiment, in order to obtain sufficient IR absorption, a length of the gas-detection waveguide 103 described in the second embodiment is set to 30 mm, and a curvature radius of the curved light waveguide 104 is set to 5 μm, so that as a total length of light waveguides, about $10^2$ m within a light waveguide type cell having a size of about 3 cm can be implemented.

Hereinafter, an analysis method using the analyzing apparatus according to the embodiment will be described.

A gas is drawn from the gas inlet port 803, and the case 800 is filled with a to-be-measured gas. A light intensity $I_0$ is obtained from the wavelength-variable light source 701. A light intensity detected by the photo-detector 703 is denoted by I. A absorbance of the gas can be obtained based on a relationship between $I_0$ and I. Furthermore, if an absorption coefficient of the gas is known, a concentration of the gas can be calculated.

Hereinafter, a principle of implementing a portable, small-sized gas analyzing apparatus according to the third embodiment will be described. In a conventional gas cell, since transmission, absorption, and spectroscopy using a spatial propagation light is used, a length thereof is in a range of several tens of centimeters to about 1 m. In addition, since optical parts such as lens need to be disposed at the front and rear stages thereof, the gas cell is very sensitive to vibration, so that the gas cell is not suitable for carrying. The light waveguide type cell 801 constituting the gas analyzing apparatus according to the embodiment together with optical fibers is disposed as a fixed part in an inner portion of the case 800. Therefore, the size thereof is less than at most about several centimeters including the case, and the length thereof is shorter by one digit or two digits. Therefore, as a matter of course, the cell can be easily carried. In addition, since the optical fibers are fixed together, the cell can be carried easily without a worry for a shift of an optical axis, similarly to general optical communication parts, for example, a semiconductor laser. In addition, the effective total optical path length is $10^2$ m, which is longer by 2 digits or more than a general spatial propagation type gas cell, so that it is possible to detect an infinitesimal gas with a higher sensitivity.

In addition, in the embodiment, in order to obtain sufficient IR absorption, a length of the gas-detection waveguide 103 is set to 30 mm, and a curvature radius of the curved light waveguide 104 is set to 5 μm, so that as a total length of light waveguides, about $10^2$ m within a light waveguide type cell 801 having a size of about 3 cm is implemented. However, the present invention is not limited thereto, but the length of the gas-detection waveguide 103, the curvature radius of the curved light waveguide 104, and the size of the element may be freely set according to a to-be-measured object. In addition, in the embodiment, although the front-stage optical fiber is used, the present invention is not limited thereto, but any structure which can be optically coupled with the light waveguide type cell 801 can be used. In addition, in the embodiment, although the wavelength-variable light source is used, instead of the wavelength-variable light source, a wide-band light source such as a super-luminescent diode or a super-continuum light may be used. In addition, in the embodiment, although the photo-detector is used, instead of the photo-detector, a component having a function of measuring both of the wavelength and the light intensity, for example, a spectrum analyzer or a combination of an array-grating type waveguide grating and a photo-detector may be used to simultaneously measure an absorption wavelength and an absorption amount with a high sensitivity, as a matter of course.

By drawing an expiratory air into the gas analyzing apparatus according to the embodiment, the gas analyzing apparatus can be used as an expiratory air analyzing apparatus. In addition, in the gas analyzing apparatus according to the embodiment, although a structure where the wavelength-variable light source 701, the light waveguide type gas cell 702, and the photo-detector 703 are combined is used, the present invention is not limited thereto. But, all these components may be integrated in a monolithic or hybrid manner.

In addition, the gas analyzing apparatus according to the embodiment and a computer may be connected to each other or a network.

The computer stores data unique to materials. For example, a molar absorption coefficient or the like may be stored. Therefore, the gas analyzing apparatus together with the computer can analyze a concentration of infinitesimal constituents contained in the gas based on the intensity of light output from the wavelength-variable light source 701 and the intensity of light detected by the photo-detector 703. In addition, a calibration curve is obtained from the intensity of light output from the wavelength-variable light source 701 and the intensity of light detected by the photo-detector 703, so that the absorption coefficient can be calculated. In addition, the obtained data may be preserved, and a change in time thereof may be examined. In this manner, the gas analyzing apparatus according to the embodiment and the computer are connected to each other, so that a gas analysis system capable of evaluating a content of analysis can be implemented. Furthermore, if the gas analyzing apparatus and the computer are connected to a network, the result of analysis can be transmitted from a site which is remotely separated from a measurement site, and the computer analyzed and the result of analysis. In addition, in the embodiment, although the light waveguide type cell 801 is disposed in an inner portion of the case 800, a wavelength-variable light source, a light waveguide type cell, and a photo-detector may be integrally disposed in a mobile phone, as a matter of course. In addition, if an expiratory air instead of the to-be-analyzed gas is drawn to the gas analysis system, concentrations of constituents contained in the expiratory air can be measured. The concentrations of gaseous constituents contained in the expiratory air are changed according to a condition or a disease. Accordingly, by using the gas analysis system, a state of health can be examined, or a disease can be diagnosed.

(Fourth Embodiment)

A fourth embodiment will be described in detail with reference to the drawings.

In the fourth embodiment, similarly to the second embodiment shown in FIG. 2, an input-light waveguide 101, an optical coupling/dividing waveguide 102, a gas-detection light waveguide 103, a curved light waveguide 104, and an output-light waveguide 105 are integrated on a substrate 100. The construction of the waveguide is the same as that of the second embodiment except for a difference to the second embodiment that high-reflectivity (HR) layers are formed on end surfaces of the input-light waveguide 101 and the output-light waveguide 105. Each of the HR layers is constructed so as to reflect a portion of the detection light and to transmit other portions thereof.

Provided that the HR layer can reflect and transmit light, the HR layer is not limited to a specific one. Therefore, half-reflective layers may be formed on different end surfaces of the input-light waveguide 101 and the output-light waveguide 105. A reflectivity of the half-reflective layer may be, for example, 90% or more or 99. 9% or more.

The HR layer is constructed by stacking multiple thin films of different materials. In terms of performance of the HR layer, it is important to lower an absorbance and a surface roughness of the HR layer.

By using a material having a low absorbance, the absorbance of the HR layer can be lowered. The material can be suitably changed in design according to a wavelength in use. For example, an oxide such as $SiO_2$ and tantalum pentoxide or a fluoride such lanthanum fluoride can be used. In the embodiment, $SiO_2$ can be most preferably used.

In order to lower the surface roughness, a film formation method may be modified. The substrate in use is polished to be a ultra-smooth surface, and a very smooth layer is deposited on the surface, so that a layer having a function of high reflection can be formed. For example, by using a sputtering method, a layer having a very smooth surface can be obtained.

Hereinafter, a principle of detection of infinitesimal gas constituents by using the light waveguide type cell according to the four embodiment of the present invention will be described. A principle of the embodiment is the same as that of the second embodiment in that transmission, absorption, and spectroscopy are available for infinitesimal gas constituents due to the light distributed in the gas phase and in that, in comparison with a conventional gas cell, a small-sized cell as a small element size of 1 digit or more can be implemented. In addition, in the embodiment, HR layers are formed on end surfaces of the input-light waveguide 101 and the output-light waveguide 105. Therefore, the light introduced from the input-light waveguide 101 into the light waveguide is reflected on the HR layers formed on the end surfaces of the output-light waveguide 105 and the input-light waveguide 101. The light reciprocally propagates with the intensity thereof slightly attenuated at every reflection. When the light is reflected by the HR layer, a portion of the light is leaked out from the HR layer. The intensity of the leaked light is decreased as an exponential function with respect to a change in time. Therefore, by plotting the intensity of the leaked light and the time, the attenuation coefficient of the light can be obtained. Since the attenuation coefficient is changed according to a concentration of the sample, the concentration of the sample can be obtained from the attenuation coefficient. In addition, a measurement result that the finally-obtained transmitted absorbed light from the output-light waveguide 105 is equivalent to the transmitted absorbed light after the propagation of an effective optical path length of about $10^5$ m can be obtained. Accordingly, a concentration of the infinitesimal sample can be obtained. For example, if HR layers having a HR-layer distance of 1 m or more and a reflectivity of about 99.9% are used, an effective optical path length of about 1000 m can be obtained. The obtained optical path length is sufficient to measure a sample having a concentration of about 10 ppm.

In addition, in the embodiment, although the HR layers are formed on different end surfaces of the input-light waveguide 101 and the output-light waveguide 105, the present invention is not limited thereto. However, the input-light waveguide 101 and the output-light waveguide 105 are formed in the same direction of the end surfaces, and the HR layers may be formed only on the end surfaces. In addition, in the embodiment, similarly to the second embodiment, the number of high mesas may be two or more, for example, three or five. In addition, the curved light waveguide 104 may be as the gas-detection light waveguide where a plurality of high mesa waveguides is disposed to be close to each other. In this case, unnecessary optical coupling/dividing waveguides therebetween may be removed. In addition, the curvature radius may be set to, for example, 25 μm or 500 μm. Furthermore, at the front stage of the input-light waveguide 101 or at the rear stage of the output-light waveguide 105, a spot size converter or a tapered light waveguide for improving connection efficiency with respect to an optical fiber may be inserted. In addition, although a length of the region of gas-detection light waveguides 103 is set to about 1 cm, the present invention is not limited thereto. The length may be set to be longer or shorter. For example, the length may be 3 cm or 1 mm. In addition, although the wavelength band in use is in the vicinity of the communication wavelength band (1.55 μm), the present invention is not limited thereto. For example, a visible light band or a mid-IR band may be used. In addition, although the optical coupling/dividing waveguide 102 is constructed with a general 1×2 optical coupling/dividing waveguide, the present invention is not limited thereto. For example, the number of branches may be changed according to the number of high mesa light waveguides. As shown in FIG. 11, the optical coupling/dividing waveguide 102 may be an optical coupling/dividing waveguide having a light distribution matching region.

Hereinafter, a method of manufacturing the light waveguide type cell according to the embodiment will be described with reference to FIGS. 6 and 7.

The manufacturing method is the same as that of the second embodiment. Firstly, an $SiO_2$ film 502 is deposited on a general SOI substrate 501 by using a thermal CVD method (see FIG. 6(a)). Next, a mask 503 is formed in a shape of waveguide by using a photolithography method using a stepper (reduced-projection exposure) (see FIG. 6(b)). Etching is performed by using the mask through an inductively-coupled plasma (ICP) method to form a high mesa 601 (see FIG. 7(a)). Next, the $SiO_2$ mask 503 on the high mesa 601 is removed by using an organic solvent and an ashing method (see FIG. 7(b)). Next, the light waveguide type cell 801 is cut, and an end surface thereof is polished. Next, multi-layered HR layers are formed on end surfaces of the input-light waveguide 101 and the output-light waveguide 105 by using a sputtering method, and after that, that the method of manufacturing the element is completed.

In addition, in the embodiment, the stepper is used for the lithography. However, the present invention is not limited thereto. For example, an electron beam exposure may be used. In addition, although the thermal CVD is used as the method of forming the $SiO_2$ film, for example, a plasma CVD method or a sputtering method may be used. In addition, the method of forming the mesa is not limited to the ICP method, but, for example, an RIE method may be used. In addition, in the embodiment, the high mesa structure where etching is performed down to the Si substrate 201 is formed. However, the etching is not necessarily performed down to the Si substrate 201, but the etching may be performed down to the Si core layer 203. In addition, in the embodiment, the light waveguide structure where the SOI substrate is used and the core layer and the clad layer are made of Si and $SiO_2$, respectively, is formed. However, the present invention is not limited thereto, but materials which basically constitute a light waveguide can be used. For example, the substrate, the clad layer, and the core layer may be made of Si, $SiO_2$, and SiN, respectively. In addition, the substrate may be made of a composite semiconductor InP, and the clad and the core layer may be made of InP and InGaAsP, respectively. As a matter of course, polymer materials may be used. In addition, in the embodiment, after the cutting of the light waveguide type cell 801, the polishing is performed. However, a cleaving process may be performed.

(Fifth Embodiment)

A fifth embodiment will be described in detail with reference to the drawings.

In the construction of the embodiment, similarly to the third embodiment shown in FIG. 8, a wavelength-variable light source 701, a light waveguide type gas cell 702, and a photo-detector 703 are connected to each other by optical fibers 704. The construction of the light waveguide type gas cell 702 is the same as that of the third embodiment shown in FIG. 9, and thus, description thereof is not repeated. The fifth embodiment is different from the third embodiment in that the light waveguide type cell 801 constituting the light waveguide type gas cell 702 is equivalent to the light waveguide type cell described in the fourth embodiment.

Hereinafter, a principle of implementing a portable, small-sized gas analyzing apparatus according to the fifth embodiment will be described. Similarly to the third embodiment, the light waveguide type gas cell 702 constituting the gas analyzing apparatus according to the embodiment together with optical fibers is disposed as a fixed part in an inner portion of the case 800. Therefore, the cell can be easily carried. In addition, since the optical fibers are fixed together, the cell can be carried easily without a worry for a shift of an optical axis, similarly to general optical communication parts, for example, a semiconductor laser. In addition, the effective total optical path length is $10^5$ m, which is longer by 5 digits or more than a general spatial propagation type gas cell, so that it is possible to detect an infinitesimal gas with a higher sensitivity.

In addition, in the embodiment, the length of the gas-detection waveguide 103, the curvature radius of the curved light waveguide 104, and the size of the element may be freely set according to a to-be-measured object. In addition, in the embodiment, although the wavelength-variable light source is used, instead of the wavelength-variable light source, a wide-band light source such as a super-luminescent diode may be used. In addition, in the embodiment, although the photo-detector is used, instead of the photo-detector, a component having a function of measuring both of the wavelength and the light intensity, for example, a spectrum analyzer or a combination of an array-grating type waveguide grating and a photo-detector may be used to simultaneously measure an absorption wavelength and an absorption amount with a high sensitivity, as a matter of course. In addition, in the embodiment, high-reflectivity mirrors are disposed on both end sources of the light waveguide type cell, and a cavity ring-down method where a pulse light is used as the input light, an attenuation time of the intensity of the pulse light with respect to the output light and a light absorption amount can be measured is applied, so that a construction capable of detecting an infinitesimal gas with a higher sensitivity can be implemented.

By drawing an expiratory air into the gas analyzing apparatus according to the embodiment, the gas analyzing apparatus can be used as an expiratory air analyzing apparatus. In addition, in the gas analyzing apparatus according to the embodiment, although a structure where the wavelength-variable light source 701, the light waveguide type gas cell 702, and the photo-detector 703 are combined is used, the present invention is not limited thereto. But, these components may be integrated in a monolithic or hybrid manner.

In addition, the gas analyzing apparatus according to the embodiment and a computer may be connected to each other or a network, so that a gas analysis system capable of processing the analyzing results can be implemented. If an expiratory air instead of an analyzing gas is drawn, unlike the embodiment where the light waveguide type cell 801 is disposed in an inner portion of the case 800, a wavelength-variable light source, a light waveguide type cell, and a photo-detector may be integrally disposed in a mobile phone, as a matter of course.

Hereinafter, an example of an analysis method using the analyzing apparatus according to the embodiment will be described.

A sample is drawn from the gas inlet port 803, and the case 800 is filled with a to-be-measured gas. A light intensity $I_0$ is obtained from the wavelength-variable light source 701. A light intensity detected by the photo-detector 703 is denoted by I. A absorbance of the sample can be obtained based on a relationship between $I_0$ and I. Furthermore, if an absorption coefficient of the sample is known, a concentration of the sample can be calculated.

(Sixth Embodiment)

A sixth embodiment will be described in detail with reference to the drawings.

Figure 10:
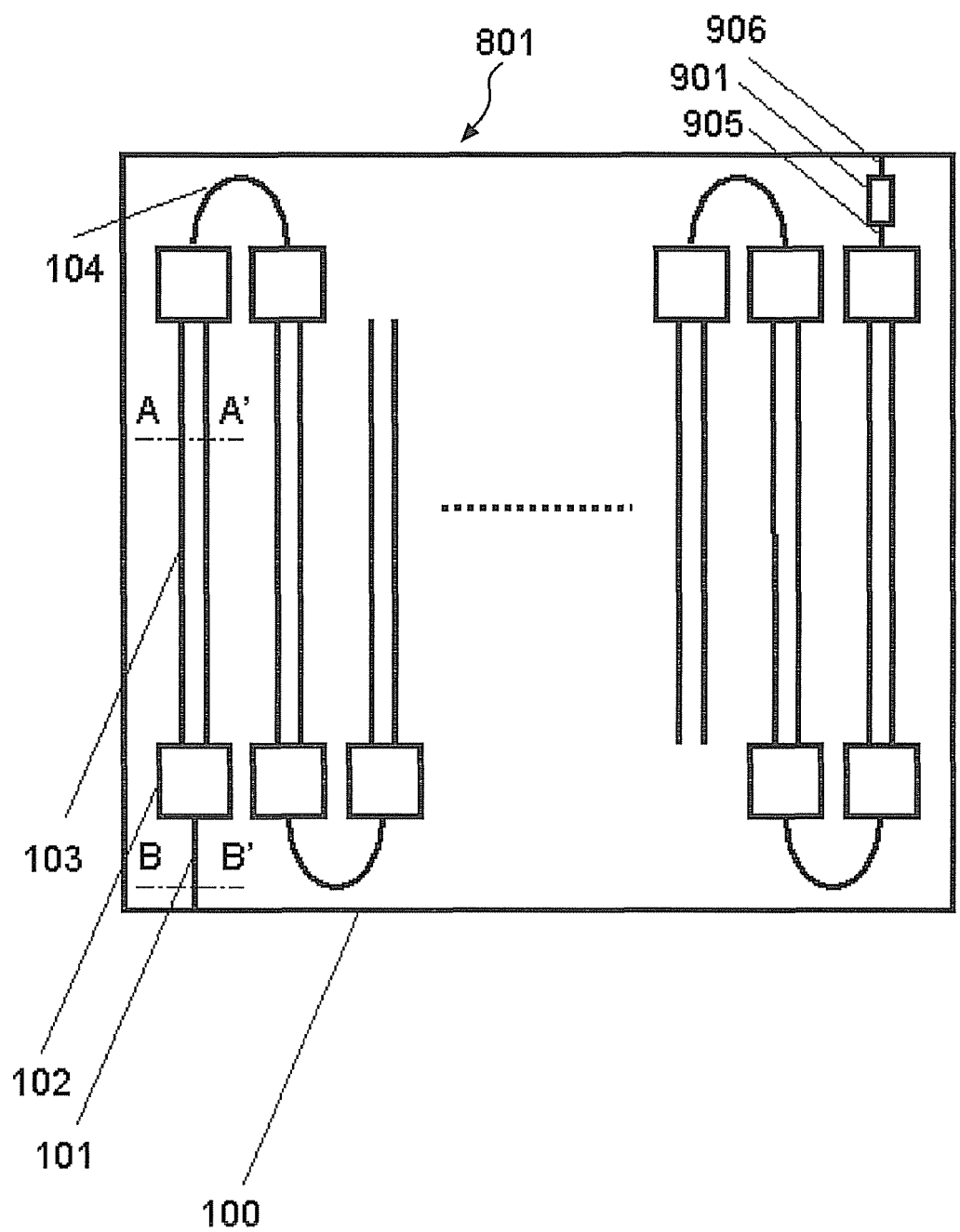
FIG. 10 is a schematic view showing a construction of the sixth embodiment.

Referring to FIG. 10, a construction of light waveguides in the light waveguide type cell according to the sixth embodiment is schematically shown. Similarly to the fourth embodiment, an input-light waveguide 101, an optical coupling/dividing waveguide 102, a gas-detection light waveguide 103, a curved light waveguide 104, a first output-light waveguide 905, and a second output-light waveguide 906 are integrated on a general SOI substrate 100. High-reflectivity (HR) layers are formed on end surfaces of the input-light waveguide 101 and the second output-light waveguide 906. In addition, a semiconductor optical amplifier 901 is integrated in a hybrid manner. The construction of the waveguide is the same as that of the fourth embodiment except for a difference to the fourth embodiment that the semiconductor optical amplifier 901 is integrated in a hybrid manner.

Hereinafter, a principle of detection of infinitesimal gas constituents by using the light waveguide type cell according to the sixth embodiment of the present invention will be described. Similarly to the second embodiment, a principle of the embodiment is the same as that of the fourth embodiment in that transmission, absorption, and spectroscopy are available for infinitesimal gas constituents due to the light distributed in the gas phase, in that, in comparison with a conventional gas cell, a small-sized cell as a small element size of 1 digit or more can be implemented, and in that the light introduced to the light waveguide is repeatedly reflected on the end surface of the output-light waveguide and the end surface of the input-light waveguide and a measurement result that is equivalent to the transmitted absorbed light after the propagation of an effective optical path length of about $10^5$ m can be obtained. In addition, in the embodiment, the semiconductor optical amplifier is integrated in a hybrid manner. Therefore, even if a large loss of propagation occurs in a light waveguide, a decrease in a measurement sensitivity due to a weakening of a signal can be avoided.

In addition, in the embodiment, similarly to the fourth embodiment, although the HR layers are formed on different end surfaces of the input-light waveguide 101 and the output-light waveguide, the present invention is not limited thereto. However, the input-light waveguide 101 and the output-light waveguide are formed in the same direction of the end surfaces, and the HR layers may be formed only on the end surfaces. In addition, in the embodiment, similarly to the fourth embodiment, the number of high mesas may be two or more, for example, three or five. In addition, the curved light waveguide 104 may be as the gas-detection light waveguide where a plurality of high mesa waveguides is disposed to be close to each other. In this case, unnecessary optical coupling/dividing waveguides therebetween may be removed. In addition, the curvature radius may be set to, for example, 25 μm or 50 μm. Furthermore, at the front stage of the input-light waveguide or at the rear stage of the output-light waveguide, a spot size converter or a tapered light waveguide for improving connection efficiency with respect to an optical fiber may be inserted. In addition, although a length of the region of gas-detection light waveguides 103 is set to about 1 cm, the present invention is not limited thereto. The length may be set to be longer or shorter. For example, the length may be 3 cm or 1 mm. In addition, in the embodiment, although the semiconductor optical amplifier 901 is integrated in a hybrid manner, instead of the semiconductor optical amplifier, a superluminescent diode may be used, and instead of the semiconductor optical amplifier 901, a Fabry-Perot type semiconductor laser may be used. Even in this case, it is possible to detect a sample with a high sensitivity. In addition, the semiconductor amplifier 501 or other light outputting devices may be inserted into any positions in an inner side of the high-reflectance plane. For example, the component may be inserted into the input-light waveguide 101 side or into a portion of the curved light waveguide 103. Furthermore, in the embodiment, although the light waveguides and the light outputting device are integrated in a hybrid manner, the present invention is not limited to the hybrid manner. For example, the light waveguides may be made of InP/InGaAsP, which is generally used, and the light outputting device may be integrated in a monolithic manner. In addition, although the wavelength band in use is in the vicinity of the communication wavelength band (1.55 μm), the present invention is not limited thereto. For example, a visible light band or a mid-IR band may be used. In addition, although the optical coupling/dividing waveguide 102 is constructed with a general 1×2 optical coupling/dividing waveguide, the present invention is not limited thereto. For example, the number of branches may be changed according to the number of high mesa light waveguides. In addition, as shown in FIG. 11, the optical coupling/dividing waveguide 102 may be an optical coupling/dividing waveguide having a light distribution matching region.

Hereinafter, a manufacturing method according to the sixth embodiment will be described with reference to FIGS. 6 and 7.

The manufacturing method is the same as that of the second embodiment. Firstly, an $SiO_2$ film 502 is deposited on a general SOI substrate 501 by using a thermal CVD method (see FIG. 6(a)). Next, a mask 503 is formed in a shape of waveguide by using a photolithography method using a stepper (reduced-projection exposure) (see FIG. 6(b)). Etching is performed by using the mask through an inductively-coupled plasma (ICP) method to form a high mesa 601 (see FIG. 7(a)). At this time, etching is performed over the entire region on which the semiconductor optical amplifier 501 is integrated. Next, the $SiO_2$ mask 503 on the high mesa 601 is removed by using an organic solvent and an ashing method (see FIG. 7(b)). Next, the light waveguide type cell 801 is cut, and an end surface thereof is polished. Next, multi-layered HR layers are formed on end surfaces of the input-light waveguide 101 and the output-light waveguide 105 by using a sputtering method, and the semiconductor optical amplifier 501 is integrated in a hybrid manner. After that, the method of manufacturing the element is completed.

In addition, in the embodiment, the stepper is used for the lithography. However, the present invention is not limited thereto. For example, an electron beam exposure may be used. In addition, although the thermal CVD is used as the method of forming the $SiO_2$ film, for example, a plasma CVD method or a sputtering method may be used. In addition, the method of forming the mesa is not limited to the ICP method, but an RIE method may be used. In addition, in the embodiment, the high mesa structure where etching is performed down to the Si substrate 201 is formed. However, the etching is not necessarily performed down to the Si substrate 201, but the etching may be performed down to the Si core layer 203. In addition, in the embodiment, the light waveguide structure where the SOI substrate is used and the core layer and the clad layer are made of Si and $SiO_2$, respectively, is formed. However, the present invention is not limited thereto, but materials which basically constitute a light waveguide can be used. For example, the substrate, the clad layer, and the core layer may be made of Si, $SiO_2$, and SiN, respectively. In addition, the substrate may be made of a composite semiconductor InP, and the clad and the core layer may be made of InP and InGaAsP, respectively. As a matter of course, polymer materials may be used. In addition, in the embodiment, although the optical amplifiers are integrated in a hybrid manner, the optical amplifiers may be integrated in a monolithic manner. In addition, in the embodiment, after the cutting of the light waveguide type cell 801, the polishing is performed. However, a cleaving process may be performed.

(Seventh Embodiment)

A seventh embodiment will be described in detail with reference to the drawings.

In the construction of the embodiment, similarly to the second embodiment shown in FIG. 8, a wavelength-variable light source 701, a light waveguide type gas cell 702, and a photo-detector 703 are connected to each other by optical fibers. The construction of the light waveguide type gas cell 702 is the same as that of the third embodiment shown in FIG. 9, and thus, description thereof is not repeated. The seventh embodiment is different from the third embodiment in that the light waveguide type cell 801 constituting the light waveguide type gas cell 702 is equivalent to the light waveguide type cell described in the sixth embodiment.

Hereinafter, a principle of implementing a portable, small-sized gas analyzing apparatus according to the seventh embodiment will be described. Similarly to the third embodiment, the light waveguide type gas cell 702 constituting the gas analyzing apparatus according to the embodiment together with optical fibers is disposed as a fixed part in an inner portion of the case 800. Therefore, the cell can be easily carried. In addition, since the optical fibers are fixed together, the cell can be carried easily without a worry for a shift of an optical axis, similarly to general optical communication parts, for example, a semiconductor laser. In addition, the effective total optical path length is $10^5$ m, which is longer by 5 digits or more than a general spatial propagation type gas cell, so that it is possible to detect an infinitesimal gas with a higher sensitivity. In addition, the optical amplifier is integrated in the light waveguide type cell 801 in a hybrid manner. Therefore, even if a large loss of propagation occurs in a light waveguide or even if a large loss to optical fibers occurs, a decrease in a measurement sensitivity due to a weakening of a signal can be avoided.

In addition, in the embodiment, the length of the gas-detection waveguide 103, the curvature radius of the curved light waveguide 104, and the size of the element may be freely set according to a to-be-measured object. In addition, in the embodiment, although the wavelength-variable light source is used, instead of the wavelength-variable light source, a wide-band light source such as a super-luminescent diode or a super-continuum light may be used. In addition, in the embodiment, although the photo-detector is used, instead of the photo-detector, a component having a function of measuring both of the wavelength and the light intensity, for example, a spectrum analyzer or a combination of an array-grating type waveguide grating and a photo-detector may be used to simultaneously measure an absorption wavelength and an absorption amount with a high sensitivity, as a matter of course. In addition, in the embodiment, high-reflectivity mirrors are disposed on both end sources of the light waveguide type cell, and a cavity ring-down method where a pulse light is used as the input light, an attenuation time of the intensity of the pulse light with respect to the output light and a light absorption amount can be measured is applied, so that a construction capable of detecting an infinitesimal gas with a higher sensitivity can be implemented. In addition, in the embodiment, although the optical amplifier is integrated in a hybrid manner, the optical amplifier may be integrated in a monolithic manner.

By drawing an expiratory air into the gas analyzing apparatus according to the embodiment, the gas analyzing apparatus can be used as an expiratory air analyzing apparatus. In addition, in the gas analyzing apparatus according to the embodiment, although a structure where the wavelength-variable light source 701, the light waveguide type gas cell 702, and the photo-detector 703 are combined is used, the present invention is not limited thereto. But, these components may be integrated in a monolithic or hybrid manner.

In addition, the gas analyzing apparatus according to the embodiment and a computer may be connected to each other or a network, so that a gas analysis system capable of processing the analyzing results can be implemented. If an expiratory air instead of an analyzing gas is drawn, unlike the embodiment where the light waveguide type cell 801 is disposed in an inner portion of the case 800, a wavelength-variable light source, a light waveguide type cell, and a photo-detector may be integrally disposed in a mobiles phone, as a matter of course.

EXAMPLE 1

A result of a quantitative analysis of a gas sample by using the light waveguide type cell 801 according to the second embodiment (see FIG. 2) was simulated.

In the light waveguide type cell 801, 30% of a total of light amount is distributed in a space between waveguides. A total length of light waveguides was set to 5 m. Ammonia-containing air samples having different concentrations (5, 10, 20 ppm) and methane-containing air samples having different concentrations (250, 500, 1000 ppm) were used. Blanks were set to air containing neither ammonia nor methane. A wavelength of an input light was set to 1.5 μm for the ammonia-containing air samples and to 1.65 μm for the methane-containing air samples. An intensity of a light output from the blanks and an intensity of a light output from each sample which absorbs light were measured. The intensity of the output light from the sample to the intensity of the output light from the blank was calculated as a decrease ratio in light intensity.

Table 1 lists the results of making the ammonia-containing air sample the samples. Table 2 lists the result of making the methane-containing air the samples.

TABLE 1

| CONCENTRATION (PPM) | DECREASE RATIO IN LIGHT INTENSITY (%) |
|---|---|
| 5 | 2.4 |
| 10 | 4.8 |
| 20 | 9.3 |

TABLE 2

| CONCENTRATION (PPM) | DECREASE RATIO IN LIGHT INTENSITY (%) |
|---|---|
| 250 | 2.4 |
| 500 | 4.8 |
| 1000 | 9.3 |

EXAMPLE 2

The light waveguide type cell 801 shown in FIG. 2 was manufactured by using the method according to the second embodiment and evaluated.

By using optical fibers, the input-light waveguide 101 was connected to the wavelength-variable light source, and the output-light waveguide 105 was connected to the photo-detector. A methane-containing air was prepared as a sample and introduced into the light waveguide type cell 801. A light having a wavelength of 1.55 μm from the wavelength-variable light source was input from the input-light waveguide 101. A light output from the output-light waveguide 105 was detected by the photo-detector. Blanks were set to a normal air containing no methane. Intensities of lights output from the sample and blanks were measured, respectively.

It could be seen from the result that the light intensity of the output light from the methane-containing air was decreased in comparison with the intensity of the output light from the blanks.

EXAMPLE 3

The light waveguide type cell 801 shown in FIG. 2 was manufactured by using the method according to the fourth embodiment and evaluated. Unlike the light waveguide type cell 801 used in Example 1, multi-layered HR layers were formed on end surfaces of the input-light waveguide 101 and the output-light waveguide 105.

By using optical fibers, the input-light waveguide 101 was connected to the wavelength-variable light source, and the output-light waveguide 105 was connected to the photo-detector. A methane-containing air was prepared as a sample and introduced into the light waveguide type cell 801. A light having a wavelength of 1.55 μm from the wavelength-variable light source was input from the input-light waveguide 101. A light output from the output-light waveguide 105 was detected by the photo-detector. Blanks were set to a normal air containing no methane. Intensities of lights output from the sample and blanks were measured, respectively.

It could be seen that the intensity of light detected by the photo-detector was decreased as an exponential function with respect to a change in time. It could be seen that the light intensity for the methane-containing air was greatly decreased in comparison with that for the blanks, and thus, an attenuation coefficient of the light was large.

Hereinbefore, the embodiments of the present invention are described with reference to the drawings. However, the embodiments are exemplary ones for the present invention. Therefore, various constructions other than those above may be employed.

In the embodiment, a gas is exemplified as a sample. However, the present invention is not limited thereto, but a mixture sample of a gas and a liquid or a liquid sample may be used.

In addition, in the embodiment, a half-open structure is exemplified for the sample chamber. However, a closed structure or a sealed structure may be used. In addition to the region interposed between parallel detection light waveguides, regions adjacent to the outer sides of the detection light waveguides may be used as a sample chamber. In other words, in the regions adjacent to the outer sides of the detection light waveguides, light absorption of the sample occurs.

An interval (width of the sample chamber) between the first and second detection light waveguides which are disposed in parallel to each other with the sample chamber interposed therebetween is suitably designed according to a refractive index of the detection light waveguides and a wavelength of a light propagating through the waveguides. By setting the interval between the waveguides to a predetermined range, optical coupling occurs, so that the light amount distributed in the sample chamber can be increased. Preferably, the interval is set to be equal to or less than a sum of the widths of the first and second detection light waveguides.

Preferably, the widths of the first and second detection light waveguides may be set to be equal to each other. If the widths of the first and second detection light waveguides are set to x and if the interval between the first and second detection light waveguides is set to d, the following is preferable.

$$x/10 \leq d \leq 2x$$

The following is more preferable.

$$x/2 \leq d \leq 3x/2$$

By doing so, the light intensity distributed in the sample chamber interposed between the two waveguides can be effectively increased. As a result, it is possible to analyze a to-be-measured sample with a high accuracy.

In the embodiment, the interval between the first and second detection light waveguides can be adjusted so as for a light distribution ratio of sample chamber to be preferably 10% or more, more preferably 20% or more. The light distribution ratio of sample chamber can be expressed by the following equation.

Light Distribution Ratio of Sample Chamber=(Light Intensity Distributed in Sample Chamber)/(Light Intensity of Propagating Light), IR absorption occurring in the propagating light is increased in proportion to the light distribution ratio of sample chamber, so that sensing can be performed with a shorter optical path length.

The invention claimed is:

1. An analyzing element comprising:
 a detection light inputting section to which a detection light is input;
 an optical divider which divides said input detection light;
 a detector to which said divided detection light is guided;
 an optical coupler which couples said detection light output from said detector; and
 a detection light outputting portion which outputs said coupled detection light,
 wherein said detector has a sample chamber into which a gas or liquid sample is introduced and first and second detection light waveguides which are disposed in parallel to each other with said sample chamber interposed therebetween, wherein each of said first and second detection light waveguides has an exposed surface which is exposed to an inner portion of said sample chamber, wherein said detection light propagating in a direction along said detection light waveguides is input to the detection light inputting portion, wherein the analyzing element further comprises a first and second units, each of which is constructed with said detector, said optical divider, and the optical coupler, wherein said first and second units are optically connected with each other, and wherein said detection light waveguide included in the first unit and said detection light waveguide included in the second unit have different light-guide directions.

2. The analyzing element as set forth in claim 1, having a light waveguide structure comprising:

a substrate; and first and second mesas, each of which is constructed with multiple layers of a lower clad layer, a core layer, and an upper clad layer which are stacked on said substrate in this order, wherein the first and second mesas are disposed in parallel to each other, wherein the core layers of said first and second mesas become said first and second detection light waveguides, and a space interposed between said first and second mesas constitutes said sample chamber, and wherein a side surface of each of said core layers is exposed to said inner portion of said sample chamber.

3. The analyzing element as set forth in claim 1, wherein said first and second units are connected with each other through a curved light waveguide.

4. The analyzing element as set forth in claim 1, wherein both of said detection light waveguides included in the first and second units have a shape of straight line and are disposed in parallel to each other.

5. The analyzing element as set forth in claim 1, wherein each of said first and second units has first and second detection light waveguides which are disposed in parallel to each other with said sample chamber interposed therebetween.

6. The analyzing element as set forth in claim 5, wherein each of said detection light inputting portion and said detection light outputting portion has a mirror, and wherein each of the mirrors is constructed so as to reflect a portion of said detection light and to transmit other portions.

7. The analyzing element as set forth in claim 6, further comprising an optical amplifier which is connected with said detection light outputting portion.

8. An analyzing apparatus including a light source, an analyzer to which a light is input from said light source, and a photo-detector which detects a light output from said analyzer, wherein said analyzer comprises the analyzing element as set forth in claim 1, and wherein said sample is analyzed based on a relationship between an intensity of the light inputting to the analyzer of said analyzing element and an intensity of the light output from the analyzer.

9. The analyzing apparatus as set forth in claim 8, wherein said analyzer further comprises an expiratory air collector which collects an expiratory air and draws the expiratory air into said sample chamber.

\* \* \* \* \*